(12) United States Patent
Schmidt et al.

(10) Patent No.: US 12,721,537 B2
(45) Date of Patent: Sep. 1, 2026

(54) SYSTEM AND METHOD FOR MEASURING BLOOD FLOW VELOCITY ON A MICROFLUIDIC CHIP

(71) Applicant: CASE WESTERN RESERVE UNIVERSITY, Cleveland, OH (US)

(72) Inventors: Bryan Schmidt, Cleveland, OH (US); Umut Gurkan, Cleveland, OH (US); Erdem Kucukal, Cleveland, OH (US); Yucheng Man, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 387 days.

(21) Appl. No.: 18/037,472

(22) PCT Filed: Nov. 17, 2021

(86) PCT No.: PCT/US2021/059740

§ 371 (c)(1),
(2) Date: May 17, 2023

(87) PCT Pub. No.: WO2022/109037

PCT Pub. Date: May 27, 2022

(65) Prior Publication Data

US 2023/0414123 A1 Dec. 28, 2023

Related U.S. Application Data

(60) Provisional application No. 63/114,904, filed on Nov. 17, 2020.

(51) Int. Cl.

| | |
|---|---|
| ***A61B 5/0285*** | (2006.01) |
| ***G06T 7/00*** | (2017.01) |
| ***G16H 30/20*** | (2018.01) |

(52) U.S. Cl.
CPC .......... *A61B 5/0285* (2013.01); *G06T 7/0016* (2013.01); *G16H 30/20* (2018.01)

(58) Field of Classification Search
CPC .... A61B 5/0285; G06T 7/0016; G16H 30/20; G01N 33/4905; G01N 27/447
See application file for complete search history.

(56) References Cited

U.S. PATENT DOCUMENTS 4,346,991 A * 8/1982 Gardner .............. A61B 3/1233 356/28.5
5,501,226 A * 3/1996 Petersen ............. A61B 3/1233 356/28.5

(Continued)

OTHER PUBLICATIONS

Yeom: Microfluidic system for monitoring temporal variations of hemorheological properties and platelet adhesion in LPS-injected rats (Year: 2017).*

(Continued)

*Primary Examiner* — Solomon G Bezuayehu
(74) *Attorney, Agent, or Firm* — Tarolli, Sundheim, Covell & Tummino LLP

(57) ABSTRACT

This application describes a microfluidic system for measuring blood flow velocity using particle image velocimetry (PIV) and wavelet-based optical flow velocimetry (wOFV) processing to determine one or more hemodynamic parameters. The hemodynamic parameters can include whole blood rheology as well as spatiotemporal variations in blood velocity, respectively, during coagulation in flowing blood samples. The system can provide quantitative information on the formation and evolution of thrombi, identify subjects with clotting disorders associated with abnormal thrombus growth rate, and/or determine the effect of therapeutics and/or therapeutical approaches on clotting dynamics and thrombus formation.

19 Claims, 9 Drawing Sheets

(56) References Cited

U.S. PATENT DOCUMENTS 6,549,801 B1* 4/2003 Chen .................... G01B 9/0201 250/350
8,834,911 B2* 9/2014 Glezer ................ A61M 1/3675 424/422
10,232,371 B2 3/2019 Collins
10,732,172 B1* 8/2020 Ingber ................ G01N 33/5064
10,803,601 B2* 10/2020 Schallek ................... G06T 1/20
11,557,042 B2* 1/2023 Thoroddsen .............. G01P 5/26
12,262,947 B1* 4/2025 Lin .......................... A61B 3/12
12,320,687 B2* 6/2025 Medeiros .............. G01F 1/7086
2003/0018275 A1* 1/2003 Tanaka ................. A61B 3/1233 600/504
2003/0149379 A1* 8/2003 Krullaards ........... A61B 5/6887 600/587
2004/0034293 A1* 2/2004 Kimball ............. A61B 5/14551 600/323
2004/0034294 A1* 2/2004 Kimball ............. A61B 5/14552 600/323
2007/0299561 A1* 12/2007 Montaser .............. B05B 12/082 250/252.1
2008/0015440 A1* 1/2008 Shandas ................... A61B 8/13 600/458
2010/0087844 A1* 4/2010 Fischer, Jr. .......... A61B 17/221 606/159
2011/0039285 A1* 2/2011 Sadaba Champetier De Ribes .... B01L 3/5027 156/219
2012/0002875 A1* 1/2012 Roth .................. G01N 15/1433 382/168
2014/0087412 A1* 3/2014 Fouras ................... G01N 11/00 435/287.1
2014/0147013 A1* 5/2014 Shandas ................ G06T 7/0016 382/107
2014/0212901 A1* 7/2014 Lowery, Jr. .......... A61B 5/0263 435/13
2015/0196688 A1* 7/2015 James ..................... A61L 27/48 623/2.12
2015/0314057 A1* 11/2015 Labib ................. B01D 63/0241 210/323.2
2016/0249874 A1* 9/2016 Korporaal ............ A61B 6/0487 382/131
2016/0278715 A1* 9/2016 Yu ........................... G06F 30/00
2017/0071516 A1* 3/2017 Bhagat ................. A61B 5/0261
2017/0227495 A1 8/2017 Gurkan et al.
2018/0185839 A1* 7/2018 Jain .................... G01N 33/4905
2018/0253854 A1* 9/2018 Falahatpisheh ........ G16H 50/30
2018/0305528 A1* 10/2018 James .................... C08K 3/011
2018/0318336 A1* 11/2018 Embury ............... A61K 31/737
2018/0321273 A1* 11/2018 Kwon ..................... G06T 7/292
2019/0090801 A1* 3/2019 Rogers ................. A61B 5/4064
2019/0114790 A1* 4/2019 Schallek ................... G06T 1/20
2020/0345323 A1* 11/2020 Weinberg .............. G01S 15/588
2021/0056867 A1* 2/2021 Basu .................... G09B 23/303
2021/0140941 A1 5/2021 Gurkan et al.
2021/0145361 A1* 5/2021 del Alamo de Pedro .................. A61B 5/4851
2021/0379359 A1* 12/2021 Schellenberg ........... A61B 8/06
2023/0210490 A1* 7/2023 He ........................... A61B 8/52 600/407
2023/0218165 A1* 7/2023 Minamide ................ A61B 3/12 600/300
2023/0414123 A1* 12/2023 Schmidt ................. G16H 30/20
2024/0366183 A1* 11/2024 Song .................... A61B 8/5207

OTHER PUBLICATIONS

Schmidt: improvements in the accuracy of wavelet-based optical flow velocimetry (wOFV) using an efficient and physically based implementation of velocity regularization (Year: 2020).*

Derian et al. "Wavelets and Optical Flow Motion Estimation", HAL Open Science, 2013. Retrieved on Jan. 17, 2022.

Kucukal et al. "Blood Flow Velocimetry in a Microchannel During Coagulation Using Particle Image Velocimetry and Wavelet-Based Optical Flow Velocimetry", ASME Journal of Biomedical Engineering, Sep. 2021. Retrieved on Jan. 17, 2020.

* cited by examiner

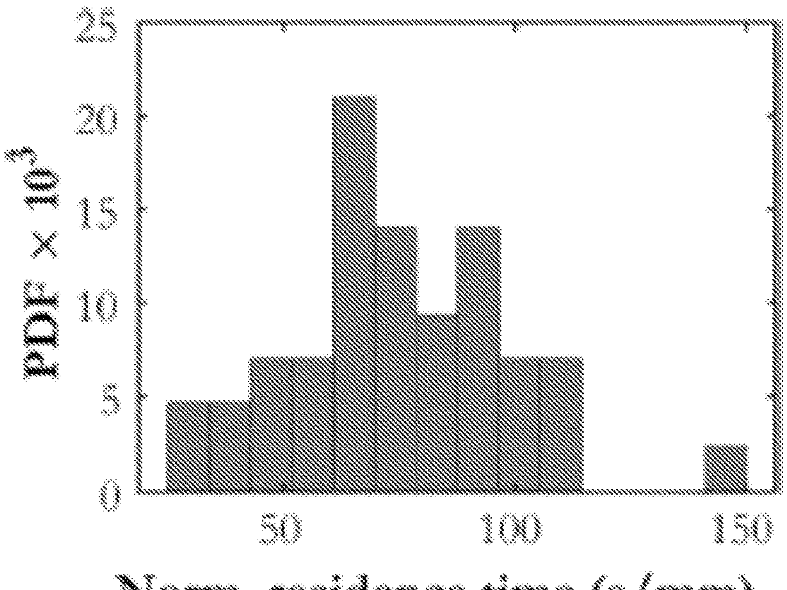
Fig. 7
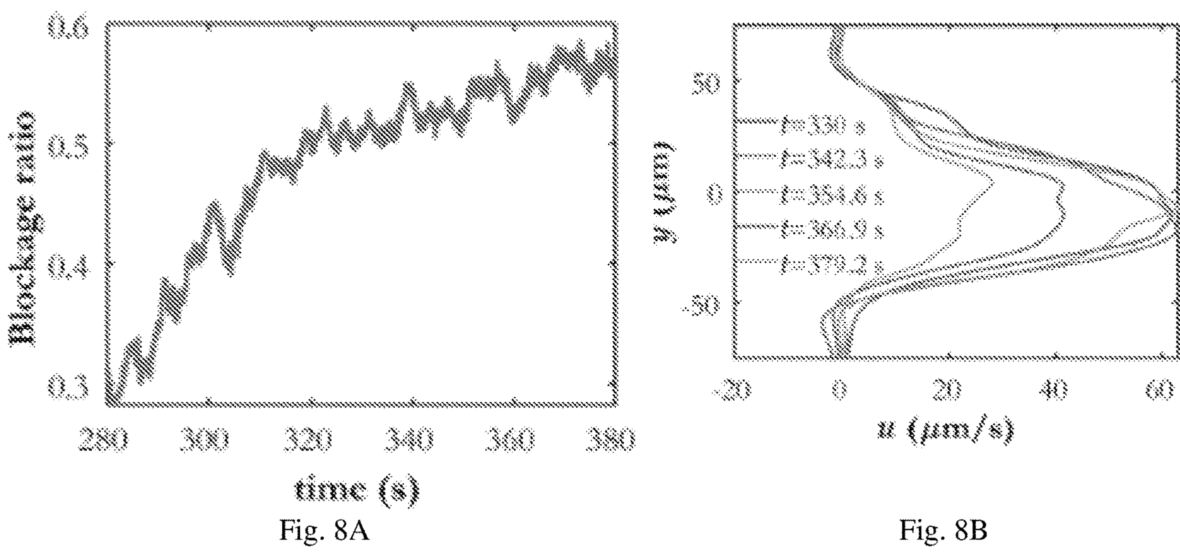
Fig. 8A
Fig. 8B

SYSTEM AND METHOD FOR MEASURING BLOOD FLOW VELOCITY ON A MICROFLUIDIC CHIP

RELATED APPLICATION

This application claims priority from U.S. Provisional Application No. 63/114,904, filed Nov. 17, 2020, the subject matter of which is incorporated herein by reference in its entirety.

GOVERNMENT FUNDING

This invention was made with government support under Grant Nos. CMMI-1552782, awarded by the National Science Foundation, and HL133574, awarded by The National Institutes of Health. The government has certain rights in the invention.

BACKGROUND

Hemostasis is a complex and multifaceted process, regulated by a series of orchestrated biochemical reactions to maintain normal blood flow through the vascular system while reacting to any vascular injuries by initiating the blood coagulation process.

The biology of blood coagulation is extremely complex and involves the interplay between many proteins and cellular structures, such as clotting factors, platelets, and red blood cells. The coagulation cascade can be triggered by either the intrinsic pathway (contact activation) or extrinsic pathway (tissue factor activation), both resulting in the formation of a thrombus due to fibrin polymerization. An imbalance in this tightly regulated system can lead to either excessive bleeding or abnormal thrombus formation, which can lead to lethal consequences if not treated.

Dynamics of blood flow plays a critical role in spatial and temporal propagation of thrombus. The local shear stress may initially increase in response to a small thrombus and significantly reduce in the event of a microvascular stenosis with a large drop in pressure. Low shear stress has been shown to induce platelet adhesion and thrombin generation downstream, which contributes to continuing growth of the thrombus. Furthermore, alteration of blood flow causes endothelial cells to possess a prothrombotic phenotype in the vicinity of the thrombus. Transportation of hemostatic proteins and cellular components is also crucial for the process of thrombus formation and largely impacted by the local flow conditions. Therefore, monitoring of temporal changes in blood flow relative to thrombus formation during a clotting process can provide unique insights in the context of hemostasis.

SUMMARY

This application describes a microfluidic system for measuring blood flow velocity using particle image velocimetry (PIV) and wavelet-based optical flow velocimetry (wOFV) processing to determine one or more hemodynamic parameters. The hemodynamic parameters can include whole blood rheology as well as spatiotemporal variations in blood velocity, respectively, during coagulation in flowing blood samples. The system can provide quantitative information on the formation and evolution of thrombi, identify subjects with clotting disorders associated with abnormal thrombus growth rate, and/or determine the effect of therapeutics and/or therapeutical approaches on clotting dynamics and thrombus formation.

The microfluidic system can include a microfluidic device in the form of a biochip having at least one microfluidic channel or microchannel through which a blood sample flows and an imaging system for measuring the velocity and/or viscosity of the blood sample. The imaging system can be used to detect temporal evolution of mean blood flow velocity by PIV, which allows calculation of clotting time and decay rate as well as blood flow velocity field by wOFV with both the velocity magnitude and streamlines being visualized. Computation of the streamlines, enabled by wOFV, allows both the identification of primary blood flow channels around thrombi and the ability to track them over time.

In some embodiments, the imaging system includes a camera configured to obtain a plurality of images of a blood sample flowing through the microchannel and a processor configured to determine one or more hemodynamic parameters based on differences between two sets of consecutive images of the plurality of images. The processor uses particle image velocimetry (PIV) of a first set of consecutive images to determine temporal evolution of mean blood flow velocity and wavelet-based optical flow velocimetry (wOFV) of a second set of consecutive images to determine a blood flow velocity field.

In an example, the PIV and wOFV processing can use images of individual blood cells of the flowing blood sample as flow tracers to estimate velocity.

In some embodiments, the processor can be configured to calculate clotting time and decay rate based on the temporal evolution of the mean flow velocity generated by PIV. The processor can also be configured to identify blood flow channels around thrombi formed in the microchannel by the velocity field generated by wOFV.

In other embodiments, the processor can be configured to pre-process the images prior to PIV and wOFV. The pre-processing can include mean filtering, intensity normalization, and edge-aware Laplacian filtering to enhance contrast. The mean filtering can reduce image noise, and the intensity normalization and edge-aware Laplacian filtering can improve motion estimation of the images.

In some embodiments, the processor is configured to segment a first image and a second image of the first set of images into a plurality of interrogation regions, cross-correlate each of the plurality of interrogation regions, and identify one more velocity vectors based on the cross-correlated interrogation regions for PIV.

In other embodiments, the processor can superimpose velocity vectors or streamlines on the blood flow velocity field determined by wOFV to determine residence time of a blood cell along flow path in the microchannel.

In some embodiments, the imaging system can include at least two cameras that provide staggered image acquisition of the blood flowing through the microchannel. For example, two cameras can be attached to a beamsplitter unit, such that each camera has an identical view of the microchannel Both cameras can operate at continuous framing but are triggered such that the second camera acquires its images a time $\Delta t$ after the images acquired by the first camera. The processor can compare images from the first camera to images of the second camera for PIV and/or wOFV.

In some embodiments, the microfluidic device includes a housing formed of gas impermeable material that includes at least one microchannel that has at least one imaging region. In some embodiments, the microchannel can include a substantially planar transparent wall that defines the upper surface or lower surface of the microchannel. The substantially planar transparent wall can permit observation into the microfluidic channel by the imaging system.

In other embodiments, the microfluidic device can include a micro-gas exchanger for controlling the oxygen content of a blood prior to and/or during perfusion of the blood through the at least one microchannel. The micro-gas exchanger can provide a blood sample under normoxic or hypoxic conditions to and/or through the at least one microchannel.

In some embodiments, the microchannel can have at least one functionalized adhesion region adapted to adhere to blood cells of interest within the blood sample. For example, at least one biological substrate (e.g., heparin, thrombin, Factor XII, etc.) and/or bioaffinity agent can be provided on and/or immobilized on a surface of the at least one microchannel. The bioaffinity agent can adhere a blood cell of interest to the at least one surface of the at least one microchannel when a blood sample containing cells is passed through the at least one microchannel. The at least one bioaffinity agent can include, for example, at least one of laminin, fibronectin, E-Selectin, P-Selectin, L-selectin, intracellular adhesion molecule 1 (ICAM-1), or vascular cellular adhesion molecule 1 (VCAM-1). The bioaffinity agent can be covalently immobilized to at least one surface of the microchannel with a cross-linker, such as GMBS.

The microfluidic system can further include a pressure pump and a reservoir that are in fluid communication with the at least one microchannel of the microfluidic device. The reservoir can include a blood sample. The pressure pump can be configured to provide pressure to the reservoir such that the blood sample flows through the at least one microchannel.

In some embodiments, the microfluidic system described herein can be used to assess the health of subjects described herein, provide quantitative information on the formation and evolution of thrombi, coagulation, and/or clotting of blood, identify subjects with clotting disorders associated with abnormal thrombus growth rate, and/or determine the effect of therapeutics and/or therapeutical approaches on clotting dynamics and thrombus formation of blood.

Other embodiments described herein relate to a method of determining one or more hemodynamic parameters of a blood sample. The method includes obtaining a video or a plurality of successive images of the blood sample flowing through a microchannel of a microfluidic device. One or more hemodynamic parameters based on differences between two sets of consecutive images of the plurality of images can be determined, wherein particle image velocimetry (PIV) of a first set of consecutive images is used to determine temporal evolution of mean blood flow velocity, and wavelet-based optical flow velocimetry (wOFV) of a second set of consecutive images is used to determine a blood flow velocity field.

In some embodiments, the flow velocity for the PIV and wOFV can be estimated by identifying individual blood cells of the flowing blood sample.

In other embodiments, clotting time and decay rate can be calculated based on the temporal evolution of the mean flow velocity determined by PIV.

In some embodiments, blood flow channels around thrombi formed in the microchannel can be identified by the velocity field generated by wOFV.

In some embodiments, one of mean filtering, intensity normalization, and edge-aware Laplacian filtering can be applied to the images prior to PIV and/or wOFV. The mean filtering can reduce image noise, and the intensity normalization and edge-aware Laplacian filtering can improve motion estimation of the images.

In some embodiments, the method can further include segmenting a first image and a second image of the first set of images into a plurality of interrogation regions, cross-correlating each of the plurality of interrogation regions, and identifying one more velocity vectors based on the cross-correlated interrogation regions for PIV.

In other embodiments, the method can further include superimposing velocity vectors or streamlines on the blood flow velocity field determined by wOFV to determine residence time of a blood cell along flow path in the microchannel.

In some embodiments, the microchannel can include at least one functionalized adhesion region adapted to adhere to blood cells of interest within the blood sample.

In some embodiments, at least two cameras can provide staggered image acquisition of the blood flowing through the microchannel. For example, two cameras can be attached to a beamsplitter unit, such that each camera has an identical view of the microchannel Both cameras can operate at continuous framing but are triggered such that the second camera acquires its images a time $\Delta t$ after the images acquired by the first camera. The processor can compare images from the first camera to images of the second camera for PIV and/or wOFV.

In any of the methods described herein, the blood sample can be perfused, for example, through one or more microfluidic channels at a sheer stress that is indicative of physiological flow, e.g., about 0.5 dyne/cm$^2$ to about 2 dyne/cm$^2$ or about 1 dyne/cm$^2$ or a predetermined pressure gradient, e.g., about 20 mBar (about 2000 Pa). Alternatively or additionally, the blood sample is perfused at a predetermined temperature, e.g., a physiologically relevant temperature.

BRIEF DESCRIPTION OF THE DRAWINGS

FIG. 7 illustrates a histogram showing normalized residence times for the streamlines shown in FIG. 6(B).

FIGS. 8(A-B) illustrate plots showing (A) temporal evolution of the computed blockage ratio, quantified by the number of streamlines that traverse a majority of the domain to the total number of seeded streamline starting locations. (B) Temporal evolution of the horizontal component of velocity along the flow channel marked with a vertical white line in FIG. 6(B). The origin on the y-axis is arbitrary.

DETAILED DESCRIPTION

Figure 1:
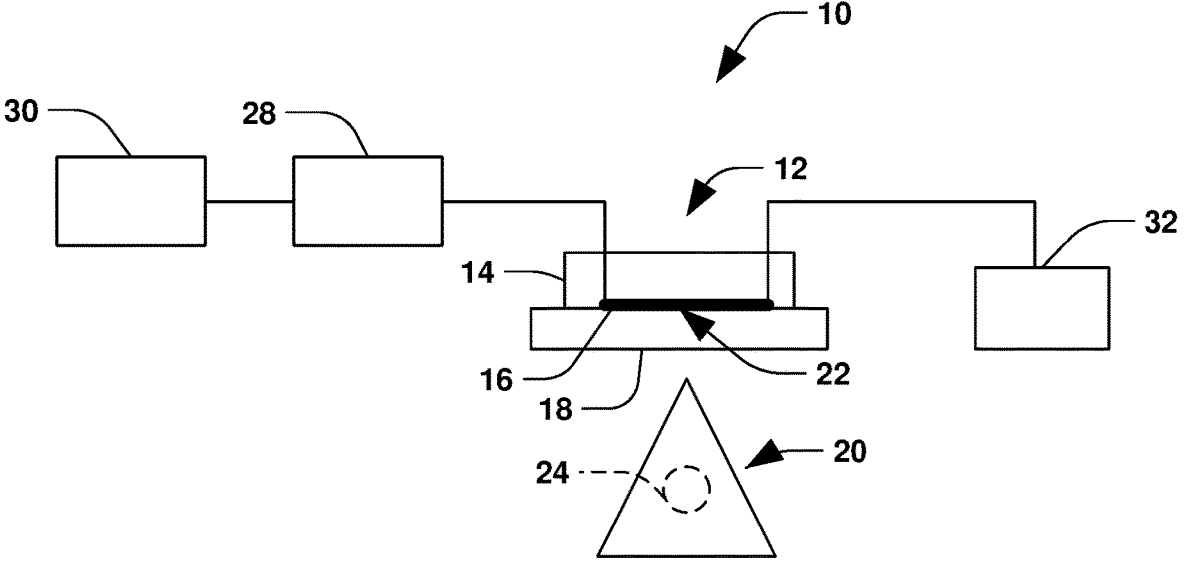
FIG. 1 is a schematic illustration of microfluidic system in accordance with an embodiment described herein.

To facilitate the understanding of this invention, a number of terms are defined below. Terms defined herein have meanings as commonly understood by a person of ordinary skill in the areas relevant to the present invention. Terms such as “a”, “an”, and “the” are not intended to refer to only a singular entity but also plural entities and also includes the general class of which a specific example may be used for illustration. The terminology herein is used to describe specific aspects of the invention, but their usage does not delimit the invention, except as outlined in the claims.

The term “microchannels” as used herein refer to pathways through a medium, e.g., silicon, that allow for movement of liquids and gasses. Microchannels can therefore connect other components, i.e., keep components “in liquid communication.” While it is not intended that the present application be limited by precise dimensions of the channels, illustrative ranges for channels are as follows: the channels can be between 0.35 and 100 μm in depth (e.g., 50 μm) and between 50 and 10,000 μm in width (e.g., 400 μm). The channel length can be between 1 mm and 100 mm (e.g., about 27 mm).

The term “microfabricated”, “micromachined”, and/or “micromanufactured” as used herein means to build, construct, assemble or create a device on a small scale, e.g., where components have micron size dimensions or microscale.

The term “polymer” as used herein refers to a substance formed from two or more molecules of the same substance. Polymers may also be linear polymers in which the molecules align predominately in chains parallel or nearly parallel to each other. In a non-linear polymer, the parallel alignment of molecules is not required.

The term “lensless image” or “lensless mobile imaging system” as used herein refers to an optical configuration that collects an image based upon electronic signals as opposed to light waves. For example, a lensless image may be formed by excitation of a charged coupled device (CCD) sensor by emissions from a light emitting diode.

The term “charge-coupled device (CCD)” as used herein refers to a device for the movement of electrical charge, usually from within the device to an area where the charge can be manipulated, for example, a conversion into a digital value. A CCD provides digital imaging when using a CCD image sensor where pixels are represented by p-doped MOS capacitors.

The term “patient” or “subject” as used herein is a human or animal and need not be hospitalized. For example, out-patients, persons in nursing homes are “patients.” A patient may comprise any age of a human or non-human animal and therefore includes both adult and juveniles, i.e., children. It is not intended that the term “patient” connote a need for medical treatment and, thus, a patient may voluntarily or involuntarily be part of experimentation whether clinical or in support of basic science studies.

The term “derived from” as used herein refers to the source of a compound or sample. In one respect, a compound or sample may be derived from an organism or particular species.

The term “functionalized” or “chemically functionalized” as used herein means the addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term “biofunctionalization,” “biofunctionalized,” or the like, as used herein, means modification of the surface of a material to have desired biological function, which will he readily appreciated by a person of skill in the related art, such as bioengineering.

The term “sample” as used herein is used in its broadest sense and includes environmental and biological samples. Environmental samples include material from the environment such as soil and water. Biological samples may be animal, including, human, fluid, e.g., blood, plasma, and serum; solid, e.g., stool; tissue; liquid foods, e.g., milk; and solid foods, e.g., vegetables. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The terms “capturing agent”, “bioaffinity ligand”, “binding component”, “molecule of interest”, “agent of interest”, “ligand” or “receptor” as used herein may be any of a large number of different molecules, biological cells or aggregates, and the terms are used interchangeably. Each capturing agent may be immobilized on a solid substrate and binds to an analyte being detected. Proteins, polypeptides, peptides, nucleic acids (nucleotides, oligonucleotides and polynucleotides), antibodies, ligands, saccharides, polysaccharides, microorganisms such as bacteria, fungi, and viruses, receptors, antibiotics, test compounds (particularly those produced by combinatorial chemistry), plant and animal cells organdies or fractions of each and other biological entities may each be a capturing agent. Each, in turn, also may be considered as analytes if same bind to a capturing agent on a microfluidic biochip.

The terms "bind" or "adhere" as used herein include any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of this application.

The term, "substrate" as used herein refers to surfaces as well as solid phases which may include a microchannel. In some cases, the substrate is solid and may comprise PDMS. A substrate may also include components including, but not limited to, glass, silicon, quartz, plastic or any other composition capable of supporting photolithography.

This application describes a microfluidic system for measuring blood flow velocity using particle image velocimetry (PIV) and wavelet-based optical flow velocimetry (wOFV) processing to determine one or more hemodynamic parameters.

Particle image velocimetry (PIV) is a fluid dynamics-based technique that measures the displacement of fluid over a finite time interval. The position of the fluid is imaged through light scattered by liquid or solid particles, such as blood cells, illuminated by a light sheet. A charge coupled device (CCD) camera sensor can be used for digital image recording where photons are converted to an electric charge based on the photoelectric effect. The light scattered by the particles is recorded on two separate frames of the CCD camera. A cross-correlation function based on Fast Fourier transform (FFT) algorithms can be used to estimate the local displacement vector of particle images between two illuminations for each area or "interrogation region" of the digital PIV recording. Based on the time interval and the image magnification from the camera calibration, a projection of the local flow velocity vector on to the plane of light sheet can then be deduced.

Wavelet-based optical flow velocimetry is a technique for determining fluid velocity in image sequences. Wavelet-based optical flow velocimetry belongs to the larger class of optical flow velocimetry (OFV) methods. The objective of OFV is to determine a velocity field from a pair of images containing some flow tracer. Like nearly every OFV approach, wOFV assumes the conservation of image intensity $I(\underline{x}, t)$ in an image sequence, i.e., I is only changed via advection by a velocity field $v(\underline{x}, t)$. The change in I thus takes the form of an advection equation, commonly encountered in fluid mechanics $$\frac{\partial I(x, t)}{\partial t} + v(x, t)\nabla I(x, t) = 0 \tag{1}$$

The unknown velocity field $\underline{v}$ is usually determined by integrating Eq. (1) in time over an interval $\Delta t = t_1 - t_0$ and performing an inverse Taylor expansion in space. This yields the displaced frame difference equation $$I_0(x) - I_1(x + v(x)\Delta t) = 0 \tag{2}$$

$\underline{v}$ is found from Eq. (2) by solving a minimization problem of the form $$v = \frac{\text{argmin}}{v} J_D(I_D, I_1, v) + \lambda J_R(v) \tag{3}$$

The two terms in Eq. (3) are the data term, $J_D$, and the regularization term, $J_R$, which are balanced by a scalar parameter 2 that is determined semi-empirically. $J_D$ is a penalty function formed from the displaced frame difference Eq. (2), and $J_R$ enforces smoothness on the velocity field. The microscale flow of a blood sample in a microchannel described herein, however, has a very small Reynolds number (Re<<1), so it is well within the regime of laminar flow. Therefore, $J_R$ is based on the Laplace operator $$J_R = \int_{\Omega} \left\| \nabla^2 v(x) \right\|^2 dx \tag{4}$$

where X is the image domain. In this form, $J_R$ penalizes the magnitude of the vector Laplacian of the velocity field via quadratic penalization. Laplacian filtering and smoothing is ubiquitous in image processing and is ideal for naturally smooth fields, such as laminar fluid flows. Wavelet-based optical flow velocimetry differs from classical OFV methods in that it does not perform the minimization in Eq. (3) over the velocity field $\underline{v}$ in the spatial domain, but rather in the wavelet domain by operating on the wavelet transform of $\underline{v}$ $$\Psi = \Psi(v) \tag{5}$$

The minimization is performed sequentially from coarse scales in the wavelet domain to finer ones, building in a natural multiresolution analysis. Additionally, regularization is performed in the wavelet domain by performing differentiation on the wavelet bases, eliminating the need for complex finite difference schemes to handle the challenging Euler-Lagrange equations resulting from Eq. (4). The estimated velocity field has one velocity vector at each pixel in the original images, and therefore wOFV can produce velocity fields with orders of magnitude higher spatial resolution compared to PIV, which produces one vector per interrogation spot.

The hemodynamic parameters determined using PIV and wOFV can include whole blood rheology as well as spatiotemporal variations in blood velocity, respectively, during coagulation in flowing blood samples. The microfluidic system can provide quantitative information on the formation and evolution of thrombi and clotting, identify subjects with clotting disorders associated with abnormal thrombus growth rate, and determine the effect of therapeutics and/or therapeutical approaches on clotting dynamics and thrombus formation in blood of a subject.

In some embodiments, the microfluidic system can include a microfluidic device in the form of a biochip having at least one microchannel through which a blood sample flows and an imaging system for measuring blood flow or velocity of the blood sample in the microchannel. The blood flow can be imaged using volumetric illumination. The images are path-integrated through the height of the microchannel, so velocimetry yields the average velocity over that height.

The imaging system can be used to detect temporal evolution of mean flow velocity by PIV, which allows calculation of clotting time and decay rate, as well as blood flow velocity field by wOFV with both the velocity magnitude and streamlines visualized. Computation of the streamlines, enabled by wOFV, allows both the identification of primary blood flow channels around thrombi or blood clots and the ability to track such thrombi or clots over time. Moreover, images of the flow field allow thrombus growth to be quantified over time, in relation to the local and average flow velocities. These parameters are expected to demonstrate a detectable unique behavior from a clinical perspective, in which people with clotting disorders may present abnormal thrombus growth rate and associated blood flow dynamics, which will be a function of total pressure drop and the shape of thrombus. The microfluidic system described here may also be utilized to evaluate the effect of emerging therapeutic approaches on clotting dynamics and thrombus formation.

In some embodiments, the imaging system includes a camera configured to obtain a plurality of successive images or video of the blood sample flowing through the microchannel and a processor configured to determine one or more hemodynamic parameters based on differences between two sets of consecutive images of the plurality of images. The processor uses particle image velocimetry (PIV) processing of a first set of consecutive images to determine temporal evolution of mean blood flow velocity and wavelet-based optical flow velocimetry (wOFV) processing of a second set of consecutive images to determine a blood flow velocity field.

In an example, the PIV and wOFV processing use images of individual blood cells of the flowing blood sample as flow tracers to estimate blood flow velocity.

In some embodiments, the processor can be configured to calculate clotting time and decay rate based on the temporal evolution of the mean flow velocity generated by PIV. The processor can also be configured to identify blood flow channels around thrombi formed in the microchannel by the velocity field generated by wOFV.

In other embodiments, the processor can be configured to pre-process the images prior to PIV and wOFV. The pre-processing can include mean filtering, intensity normalization, and edge-aware Laplacian filtering to enhance contrast. The mean filtering can reduce image noise, and the intensity normalization and edge-aware Laplacian filtering can improve motion estimation of the images.

In some embodiments, the processor is configured to segment a first image and a second image of the first set of images into a plurality of interrogation regions, cross-correlate each of the plurality of interrogation regions, and identify one more velocity vectors based on the cross-correlated interrogation regions for PIV.

In other embodiments, the processor can superimpose velocity vectors or streamlines on the blood flow velocity field determined by wOFV to determine residence time of a blood cell along flow path in the microchannel.

In some embodiments, the imaging system can include at least two cameras that provide staggered image acquisition of the blood flowing through the microchannel. For example, two cameras can be attached to a beamsplitter unit, such that each camera has an identical view of the microchannel Both cameras can operate at continuous framing but are triggered such that the second camera acquires its images a time $\Delta t$ after the images acquired by the first camera. The processor can compare images from the first camera to images of the second camera for PIV and/or wOFV.

In some embodiments, the microfluidic device includes a housing formed of gas impermeable material that includes at least one microchannel that has at least one imaging region. In some embodiments, the microchannel can include a substantially planar transparent wall that defines an upper surface or lower surface of the microchannel. The substantially planar transparent wall can permit observation into the microfluidic channel by the imaging system.

In other embodiments, the microfluidic device can include a micro-gas exchanger for controlling the oxygen content of a blood prior to and/or during perfusion of the blood through the at least one microchannel. The micro-gas exchanger can provide a blood sample under normoxic or hypoxic conditions to and/or through the at least one microchannel.

In some embodiments, the microchannel can have at least one functionalized adhesion region adapted to adhere to blood cells of interest within the blood sample. For example, at least one biological substrate (e.g., heparin, thrombin, Factor XII, etc.) and/or bioaffinity agent can be provided on and/or immobilized on a surface of the at least one microchannel. The bioaffinity agent can adhere a cell of interest to the at least one surface of the at least one microchannel when a blood sample containing cells is passed through the at least one microchannel. The at least one bioaffinity agent can include, for example, at least one of laminin, fibronectin, E-Selectin, P-Selectin, L-selectin, intracellular adhesion molecule 1 (ICAM-1), or vascular cellular adhesion molecule 1 (VCAM-1). The bioaffinity agent can be covalently immobilized to at least one surface of the microchannel with a cross-linker, such as GMBS.

The microfluidic system can further include a pressure pump and a reservoir that are in fluid communication with the at least one microchannel of the microfluidic device. The reservoir can include a blood. The pressure pump can be configured to provide pressure to the reservoir such that the blood sample flows through the at least one microchannel.

In some embodiments, the microfluidic system described herein can be used to assess the health of subjects, provide quantitative information on the formation and evolution of thrombi, coagulation, and/or clotting in blood, identify subjects with clotting disorders associated with abnormal thrombus growth rate, and/or determine the effect of therapeutics and/or therapeutical approaches on clotting dynamics and thrombus formation.

FIG. 1 illustrates a schematic view of a microfluidic system 10 in accordance with an embodiment described herein. The microfluidic system 10 includes a microfluidic device or biochip 12 that has a gas impermeable housing 14 and at least one microchannel 16 in the housing 14. The microchannel 16 can be coupled to a constant pressure pump 30 that provides a physiologically relevant pressure value (e.g., about 20 mBar) to flow or perfuse a blood sample that is contained in a reservoir 28 through the housing 14. The at least one microchannel 16 can be connected to the reservoir 28 by inlet silicone tubing and male luer connectors.

The housing 14 including the at least one microchannel 16 can further contain a substantially planar transparent wall 18 that defines a surface of at least one of the microchannels 16. This substantially planar transparent wall 18, which can be, for example, glass or plastic, permits observation into the microfluidic channel 16 by an imaging system 20 (e.g., microscopy) so that at least one measurement of blood that passes through the microchannel of one of the microfluidic channels 16 can be obtained. In one example, the transparent wall has a thickness of 0.05 mm to 1 mm. In some cases, the transparent wall 18 may be a microscope cover slip, or similar component. Microscope coverslips are widely available in several standard thicknesses that are identified by numbers, as follows: No. 0-0.085 to 0.13 mm thick, No. 1-0.13 to 0.16 mm thick, No. 1.5-0.16 to 0.19 mm thick, No. 2-0.19 to 0.23 mm thick, No. 3-0.25 to 0.35 mm thick, No. 4-0.43 to 0.64 mm thick, any one of which may be used as a transparent wall 18, depending on the device, microscope, and detection strategy.

In some embodiments, the microfluidic channel(s) 16 may have a depth or height in a range of 0.5 μm to 100 μm, 0.1 μm to 100 μm, 1 μm to 50 μm, 1 μm to 50 μm, 10 μm to 40 μm, 5 μm to 15 μm, 0.1 μm to 5 μm, or 2 μm to 5 μm. The microfluidic channel(s) may have a depth or height of up to 0.5 μm, 1 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 20 μm, 30 μm, 40 μm, 50 μm, 75 μm, 100 μm, or more.

In some embodiments, the at least one microchannel 16 can have a cross-sectional area, perpendicular to the flow direction, of 1 $\mu m^2$, 10 $\mu m^2$, 20 $\mu m^2$, 30 $\mu m^2$, 40, $\mu m^2$, 50 $\mu m^2$, 60 $\mu m^2$, 70 $\mu m^2$, 80 $\mu m^2$, 90 $\mu m^2$, 100 $\mu m^2$, 150 $\mu m^2$, 200 $\mu m^2$, 300 $\mu m^2$, 400 $\mu m^2$, 500 $\mu m^2$, 600 $\mu m^2$, 700 $\mu m^2$, 800 $\mu m^2$, 900 $\mu m^2$, 1000 $\mu m^2$, or more.

The microfluidic device 10 may be designed and configured to have a channel cross-sectional area, perpendicular to the flow direction, in a range of 1 μm 2 to 10 $\mu m^2$, 10 $\mu m^2$ to 50 $\mu m^2$, 50 μm 2 to 100 μm 2 μm 2 to 500 $\mu m^2$, 500 μm 2 to 1500 $\mu m^2$, for example.

The microfluidic device 10 may be designed and configured to produce any of a variety of different shear rates (e.g., up to 100 dynes/cm 2). For example, the microfluidic device 10 may be designed and configured to produce a shear rate in a range of 0.1 dynes/$cm^2$ to 10 dynes/$cm^2$, 0.5 dynes/$cm^2$ to 5 dynes/$cm^2$, 0.5 dynes/$cm^2$ to 2 dynes/$cm^2$, 0.6 dynes/$cm^2$ to 1.5 dynes/$cm^2$, 0.7 dynes/cm 2 to 1.3 dynes/$cm^2$, 0.8 dynes/$cm^2$ to 1.2 dynes/$cm^2$, or 0.9 dynes/$cm^2$ to 1.1 dynes/$cm^2$, or 1 dynes/$cm^2$.

The microchannel 16 can have a constant width or a width that continuously changes in a direction of the fluid sample flow through the microchannel. Varying the microchannel width provides continuously changing shear rates (shear gradient) along its length. Providing a shear gradient along the flow direction allows for the investigation of shear-dependent adhesion of cells, clotting, and thrombus formation at a single flow rate. The microchannel geometry can be configured such that both the mean flow velocity and shear stress decrease along the flow direction while the flow rate is constant.

In some embodiments, the microfluidic system 10 can simulate physiologically relevant shear gradients (e.g., 0.5 dynes/$cm^2$ to about 2 dynes/$cm^2$) of microcirculatory blood flow at a constant single volumetric flow rate. Using this system, shear-dependent adhesion and deformability of cells, for example, red blood cells (RBCs) and white blood cells (WBCs) as well as blood clotting or coagulation from subjects with clotting disorders, such can be investigated to determine thrombi formation.

The microchannel 16 optionally includes at least one cell adhesion region 22 within the microchannel 16. The optional cell adhesion region 22 of the microchannel 16 can be functionalized with at least one capturing agent that captures or adheres a blood cell of interest to a surface of the microchannel when a blood sample containing cells is passed or perfused through the at least one microchannel. If the housing includes multiple microchannels, each microchannel can be functionalized with a different capturing agent to adhere different cells of interest thereto. In any case, each microchannel is configured to receive and provide cell adhesion analysis of a microvolume blood sample.

In some embodiments, the capturing agents can include, for example, bioaffinity ligands or adhesion molecules that are associated with an activated phenotype associated with a vaso-occlusive disorder. Such bioaffinity ligands or adhesion molecules can include, for example, E-Selectin, P-Selectin, intracellular adhesion molecule 1 (ICAM-1) and vascular cellular adhesion molecule 1 (VCAM-1). E-selectin and P-selectin are expressed on the surfaces of endothelial cells in response to inflammatory stimuli and mediates leukocyte rolling and adhesion on endothelial cells. ICAM-1 and VCAM-1 are also expressed on the surface of endothelial cells in response to inflammatory stimuli and helps regulate inflammation associated cellular adhesion and transmigration of WBCs. VCAM-1 further mediates adhesion of sickle RBCs, particularly reticulocytes, which are young RBCs. E-Selectin, P-Selectin, ICAM-1, and/or VCAM-1 can adhere to cells, such as WBCs and/or RBCs, and be used to detect and/or measure WBC and/or RBC adherence under physiological relevant shear stress and normoxic and hypoxic conditions.

In other embodiments, the capturing agent can include, for example, cells, such as endothelial cells, including human umbilical vein endothelial cells and human pulmonary microvessel endothelial cells, that can potentially adhere to cells, such as WBCs adhesion and/or RBCs under physiological relevant shear stress and normoxic and hypoxic conditions. The cells, e.g., endothelial cells, can be adhered or functionalized to the surface of the cell adhesion region of the blood flow in the microchannel and cultured under physiological relevant flow conditions. The cultured cells, such as cultured endothelial cell can be activated with a variety of stimuli including heme, TNF-α, hydrogen, peroxide, and thrombin to mimic various physiological or pathological conditions.

The microfluidic system 10 also includes an imaging system 20 for measuring blood flow or velocity of the blood sample in the microchannel. The imaging system 20 can be a lens-based imaging system, lensless imaging system, and/or mobile imaging system, e.g., cellular phone camera. In some embodiments, the imaging system 20 can include a control unit 24, which can a include a computer readable storage unit and a processor to analyze the images of the microchannels and provide real-time feedback to a subject of the results of the image acquisition/analysis. These results, in turn, can be readily transmitted to a primary care provider and/or stored in a medical record database.

In some embodiments, the imaging system 20 includes a camera, such as a charge-coupled device (CCD) camera coupled to a microscope, and a processor. The camera can be configured to obtain a plurality of successive images or video of the blood sample flowing through the microchannel 16. In some embodiments, the camera can be coupled to a microscope objective positioned relative to the microchannel 16 so that the entire flow domain of the microchannel 16 is illuminated. Illumination of the entire flow domain allows images and velocity measurements to be obtained that can provide a two-dimensional (2D) velocity vector map, which contains information throughout the entire flow domain. The 2D velocity vectors represent the average values for the 3D flow.

By way of example, blood flow imaging can be performed by rinsing the assembled microfluidic channels with 100% ethanol and PBS. A microfluidic flow control system can be used to regulate the flow pressure in the microfluidic channels. For each measurement, a 500 μL whole blood sample can be loaded into the input reservoir and perfused at a constant pressure of 20 mBar, and videos are recorded. Data acquisition can begin after the initiation of flow to allow it to reach a steady state.

The processor can be configured to determine one or more hemodynamic parameters based on differences between two sets of consecutive images of the plurality of successive images or video obtained by the camera. Series of successive images can extracted from the videos or successive images and analyzed by the processor, which can include image analysis software and algorithms specifically developed for velocimetry.

The processor can use particle image velocimetry (PIV) processing of a first set of consecutive images to determine temporal evolution of mean blood flow velocity and wavelet-based optical flow velocimetry (wOFV) processing of a second set of consecutive images to determine a blood flow velocity field. Commercial PIV software (e.g., Insight 4G) can be applied to consecutive frames from the image sequences to determine velocity. The resulting velocity field is rather coarse in terms of spatial resolution compared to the images, but PIV is able to resolve large inter-frame displacements of RBCs between consecutive images, so it is suited to the task of determining parameters based on the average velocity over the entire spatial domain, such as clotting time and decay rate. wOFV is restricted to small inter-frame displacements, but it offers spatial resolution equal to the image resolution, an enhancement of more than two orders of magnitude compared to PIV, and it is more accurate than PIV when large spatial velocity gradients are present, such as when channels of flow form around thrombi. Therefore, wOFV measurements are used to make detailed investigations of coagulation dynamics and thrombi formation.

The velocity fields from PIV and wOFV can be further analyzed by the processor to determine the hemodynamic parameters relevant to coagulation. These parameters are expected to vary between individual patients, particularly among those with blood disorders, and under the influence of microchannel coatings or therapeutic agents.

The imaging system 20 can be used to detect temporal evolution of mean flow velocity by PIV, which allows calculation of clotting time and decay rate, as well as blood flow velocity field by wOFV with both the velocity magnitude and streamlines visualized. Computation of the streamlines, enabled by wOFV, allows both the identification of primary blood flow channels around thrombi and the ability to track thrombi formation, clotting, and coagulation over time. The imaging system can optionally measure the deformability, morphology, and/or quantity of blood cells of interest in the microchannel when the blood sample is passed or perfused through the microchannel under, for example, physiological relevant shear stress and normoxia or hypoxia conditions.

In some embodiments, the images can be sent to control unit that includes a computer readable storage medium for storing the images and a processor that include executable instructions for receiving sequential images, generating general velocity vector maps based on successive images, and generating mean flow velocity data from the velocity vector maps using PIV and wOFV. The mean flow velocity data can be output from the processor to a display as raw data or as visual representation of the mean flow velocity. The mean flow velocity data or map can be correlated to viscosity, coagulation, thrombi formation, and/or clotting of the blood using the processor or another processor that outputs the data of the blood flow as raw data or as visual depiction.

The image processing may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) can be encoded with one or more programs that, when executed on one or more computers or other processors, perform methods that implement the various embodiments described herein. The computer readable medium or media can be transportable, such that the program or programs stored thereon can be loaded onto one or more different computers or other processors to implement various aspects described herein. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects as discussed above. Additionally, it should be appreciated that according to one aspect of this embodiment, one or more computer programs that when executed perform methods of described herein need not reside on a single computer or processor, but may be distributed in a modular fashion amongst a number of different computers or processors to implement various aspects herein.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

In an example, the PIV and wOFV can use images of individual blood cells of the flowing blood sample as flow tracers to estimate blood flow velocity.

In some embodiments, the processor can be configured to calculate clotting time and decay rate thrombi or clots based on the temporal evolution of the mean flow velocity generated by PIV. The processor can also be configured to identify blood flow channels around thrombi formed in the microchannel by the velocity field generated by wOFV.

In other embodiments, the processor can be configured to pre-process the images prior to PIV and wOFV, wherein the pre-processing includes mean filtering, intensity normalization, and edge-aware Laplacian filtering to enhance contrast. The mean filtering can reduce image noise, and the intensity normalization and edge-aware Laplacian filtering can improve motion estimation of the images.

In some embodiments, the processor is configured to segment a first image and a second image of the first set of images into a plurality of interrogation regions, cross-correlate each of the plurality of interrogation regions, and identify one more velocity vectors based on the cross-correlated interrogation regions for PIV.

In other embodiments, the processor can superimpose velocity vectors or streamlines on the blood flow velocity field determined by wOFV to determine residence time of a blood cell along flow path in the microchannel.

Figure 10:
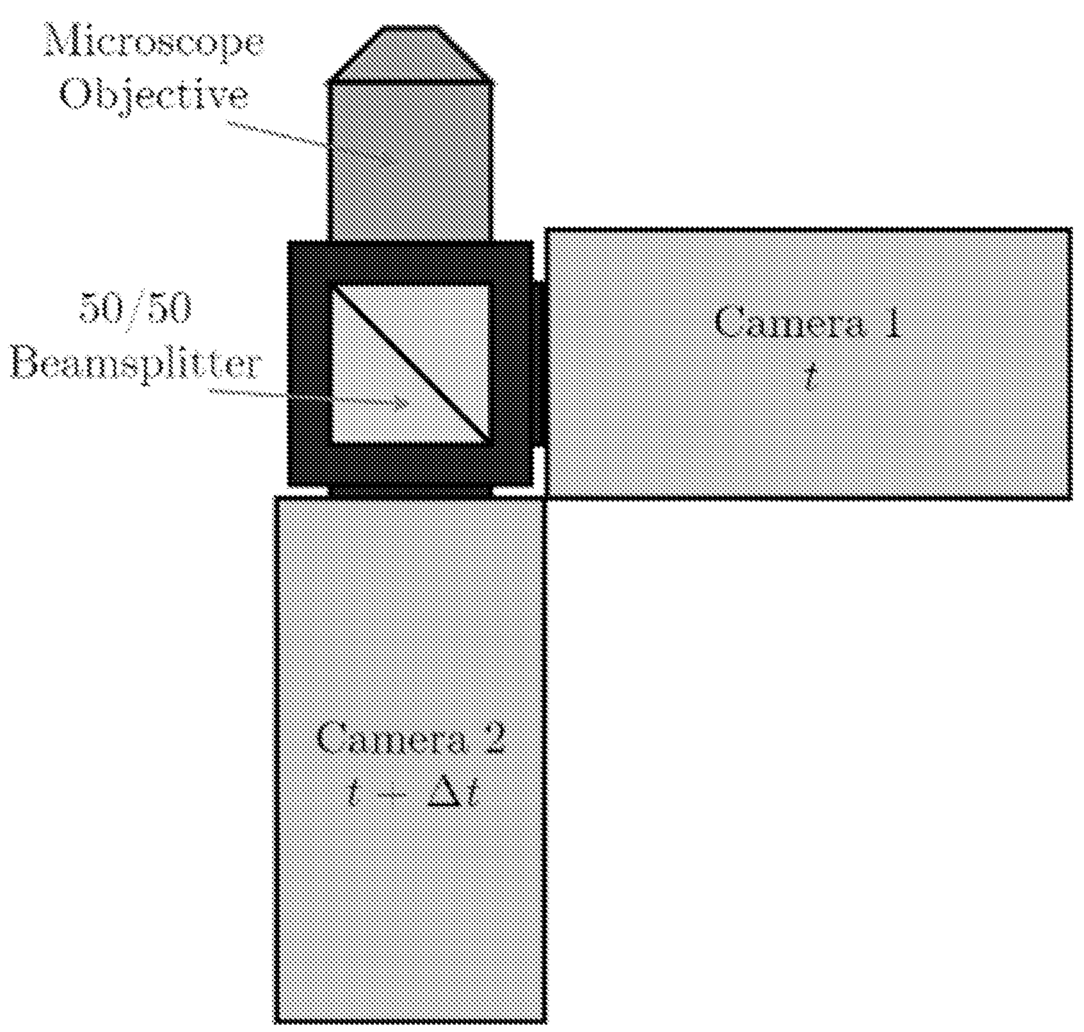
FIG. 10 illustrates the proposed two-camera system for recording image pairs for velocity analysis. The same image is projected to both cameras via a 50/50 beamsplitter cube, but the cameras are triggered with a delay of $\Delta t$ between them. In this way, the inter-frame displacement of the RBCs can be precisely controlled by specifying the time delay. Each camera records at a continuous rate, but pairs of images from Cameras 1 and 2 are separated by an arbitrarily short time and are used for estimating the velocity.

In some embodiments, as illustrated in FIG. 10, the imaging system can include at two cameras that provide staggered image acquisition of the blood flowing through the microchannel. For example, two cameras can be attached to a beamsplitter unit, such that each camera has an identical view of the microchannel. Both cameras can operate at continuous framing but are triggered such that the second camera acquires its images a time Δt after the images acquired by the first camera. The processor can compare images from the first camera to images of the second camera for PIV and/or wOFV.

In some embodiments, the reservoir 28, which is fluidically connected to the one or more microfluidic channels 16 and the pump 30, can perfuses blood from the reservoir 28 through the one or more microchannels 16 to a waste reservoir 32. The pump 30 can designed and configured to create a pressure to create a pressure (gauge pressure) in at least one of the microchannels 16 of up to 50 Pa, 100 Pa, 200 Pa, 300 Pa, 400 Pa, 500 Pa, 600 Pa, 700 Pa, 800 Pa, 900 Pa, 1 kPa, 2 kPa, 5 kPa, 10 kPa or more. The pump 30 may be designed and configured to create a pressure (gauge pressure) in the channel in a range of 10 Pa to 2000 Pa, 100 Pa to 5000 Pa, 100 Pa to 8000 Pa, 100 Pa to 10 kPa, 500 Pa to 5 kPa, or 500 Pa to 10 kPa.

The microfluidic system 10 may also be designed and configured to create an average fluid velocity within the channel of up to 1 μm/s, 2 μm/s, 5 μm/s, 10 μm/s, 20 μm/s, μm/s, 100 μm/s, or more.

The microfluidic system 10 may be designed and configured to create an average fluid velocity within at least one microchannel 16 in a range of 1 μm/s to 5 μm/s, 1 μm/s to 10 μm/s, 1 μm/s to 20 μm/s, 1 μm/s to 50 μm/s, 10 μm/s to 100 μm/s, or 10 μm/s to 200 μm/s, for example.

In any of the methods described herein, the blood sample can be perfused, for example, through one or more microfluidic channels at a sheer stress that is indicative of physiological flow, e.g., about 0.5 dyne/cm$^2$ to about 2 dyne/cm$^2$ or about 1 dyne/cm$^2$ or a predetermined pressure gradient, e.g., about 20 kPa. Alternatively or additionally, the fluid is perfused at a predetermined temperature, e.g., a physiologically relevant temperature.

In some embodiments, the reservoir 28 contains blood or plasma that includes cells, such as RBCs and WBCs, suspended in the blood or plasma.

In some embodiments, the cells can be RBCs, WBCs, stem cells, cancer cells, epithelial cells (e.g., epithelial cells of the cervix, pancreas, breast or bladder), B cells, T cells, or plasma cells that can be obtained from a subject having or is suspected of having a disease (e.g., diabetes, infection with a virus such as HIV, anemia, a hematological cancer, such as leukemia, a spleen disease, multiple myeloma, monoclonal gammopathy of undetermined significance, sickle cell disease, or spherocytosis).

In some embodiments, the microfluidic system 10 can further includes a micro-gas exchanger (not shown) fluidly connected to the at least one microchannel 16 for varying the oxygen content of the fluid sample containing the cells. The micro-gas exchanger can include a gas-permeable inner tube inserted within a gas-impermeable outer tube. Blood containing the cells of interest can be delivered through the inner tube such that the fluid exchanges gases through the permeable tubing wall with a control gas, e.g., 5% $CO_2$ and 95% $N_2$, between the tubes. The oxygen content of the fluid exiting the micro-gas exchanger is controlled to thereby control the oxygen content of the fluid delivered to the microchannel.

By way of example, the micro-gas exchanger can include concentric inner and outer tubes. The inner tube has a gas-permeable wall defining a central passage extending the entire length of the inner tube. The outer tube has a gas impermeable wall defining a central passage extending the entire length of the outer tube. An annular space is formed between the tubes. The central passage receives the fluid sample and is in fluid communication with one or more inlet ports of the microfluidic device. Each inlet port can be fluidly connected to the same micro-gas exchanger or a different micro-gas exchanger to specifically tailor the fluid delivered to each microchannel. An outlet tube is connected to each outlet port of the micro-gas exchanger. A controlled gas flow takes place in the annular space between the concentric tubes and fluid flows inside the inner tube. When the fluid sample is blood, deoxygenation of the sample occurs due to gas diffusion (5% $CO_2$ and 95% $N_2$) through the inner gas-permeable wall.

The microfluidic system described herein can foster a new understanding of the coagulation process and the role played by fluid dynamics, and be used to develop new diagnostic capabilities for vascular diseases. The microfluidic system described herein can provide fundamental knowledge as well as experimental, computational, and modeling tools to better understand a critical biological function that is impacted by diseases and conditions, such as diabetes, obesity, anemias, hypertension, cancer, blood transfusion complications, heart disease, and certain conditions such as sepsis. These diseases affect hundreds of millions of people globally with a socioeconomic burden of hundreds of billions of dollars annually. Socioeconomically, the microfluidic system described herein can lead to improved diagnosis and evaluation of health conditions and treatments, enhancing patient quality of life and reducing morbidity and mortality, while simultaneously lowering healthcare costs by helping health care providers better tailor treatments to individual patients.

The microfluidic system described herein integrated with PIV and wOFV holds great promise for potential future applications from a clinical perspective. For example, assessment of clotting time and decay rate of thrombi or clots for a clinically diverse patient population can enable monitoring of disease status and the impact of therapeutical interventions on variations in these parameters. More importantly, functionalization of microchannel surface via relevant biological substrates (e.g., heparin, thrombin, Factor XII, etc.) may alter fluid dynamics and thrombus formation in a patient-specific fashion and warrants further research. Further, the efficacy of emerging therapies against thrombus-targeting fibrinolysis can be quantitatively evaluated under physiologically relevant shear conditions using this approach.

Further, the microfluidic system described herein can provide for measurement of coagulation and thrombi formation, in combination with cell adhesion or deformability of the cell population. The combination of determining measurement of coagulation or thrombi formation and cytoadhesive properties and the deformative properties of a cell population, particularly a blood cell population containing a plurality of different cell types (e.g., RBCs and WBCs), may be used to generate a "Health Signature" that comprises an array of properties that can be tracked in a subject over a period of time. Such a Health Signature may facilitate effective monitoring of a subject's health over time. Such monitoring may lead to an early detection of potential acute or chronic infection, or other disease, disorder, fitness, or condition.

In some embodiment, the adherence of blood cells, such as RBCs and WBCs, to various capturing agents, such as E-Selectin, P-Selectin, ICAM-1, VCAM-1, and/or endothelial cells, provided in the microchannels of the microfluidic device devices can be used for evaluating, assessing, monitoring, and/or predicting disease status, disease prognosis, treatment course (e.g., therapeutic selection, dosing schedules, administration routes, etc.), response to treatment and/or treatment efficacy.

In some embodiments, the microfluidic device described herein can be used to assess the health of any of the subjects described herein, used to detect or determine the stage of any of the diseases or conditions described herein and can be used for determining the number of diseased versus healthy cells.

In other embodiments, a method for detecting a condition or disease in a subject can include obtaining blood, from the subject, perfusing a blood sample containing cells through the microfluidic channel, and obtaining a video or plurality of successive images of the blood sample flowing through a microchannel of a microfluidic device. One or more hemodynamic parameters based on differences between two sets of consecutive images of the plurality of images can be determined, wherein particle image velocimetry (PIV) of a first set of consecutive images is used to determine temporal evolution of mean blood flow velocity and wavelet-based optical flow velocimetry (wOFV) of a second set of consecutive images is used to determine a blood flow velocity field.

In some embodiments, the blood can be obtained directly or indirectly by acquiring a blood sample from a subject. For example, a blood sample may be obtained (e.g., at a point-of-care facility, e.g., a physician's office, a hospital, laboratory facility) by procuring a tissue or fluid sample (e.g., blood draw, marrow sample, spinal tap) from a subject. Alternatively, a blood sample may be obtained by receiving the blood sample (e.g., at a laboratory facility) from one or more persons who procured the sample directly from the subject.

Blood flow velocity fields generated using PIV and wOFV processing of images the blood flow in the microchannel of the microfluidic device can then be determined and compared to a standard or control to indicate whether the subject has the condition or disease; and optionally, diagnosing the subject as having the condition or disease based on the results. The appropriate standard or control can be the blood flow velocity and/or coagulation of blood obtained from a subject who is identified as not having the condition or disease. The blood flow velocity in the microchannel can also be measured and compared to a control or standard to indicate or further characterize whether the subject has the condition or disease.

An "appropriate standard" is a parameter, value or level indicative of a known outcome, status or result (e.g., a known disease or condition status). An appropriate standard can be determined (e.g., determined in parallel with a test measurement) or can be pre-existing (e.g., a historical value, etc.). The parameter, value or level may be, for example, a flow or adherence characteristic (e.g., flow time). For example, an appropriate standard may be the flow or adherence characteristic of a blood cell obtained from a subject known to have a disease, or a subject identified as being disease-free. In the former case, a lack of a difference between the flow or adherence characteristic and the appropriate standard may be indicative of a subject having a disease or condition. Whereas in the latter case, the presence of a difference between the flow or adherence characteristic and the appropriate standard may be indicative of a subject having a disease or condition. The appropriate standard can also be a mechanical property or rheological property of a cell obtained from a subject who is identified as not having the condition or disease or can be a mechanical property or rheological property of a cell obtained from a subject who is identified as having the condition or disease.

The magnitude of a difference between a parameter, level or value and an appropriate standard that is indicative of known outcome, status or result may vary. For example, a significant difference that indicates a known outcome, status or result may be detected when the level of a parameter, level or value is at least 1%, at least 5%, at least 10%, at least 25%, at least 50%, at least 100%, at least 250%, at least 500%, or at least 1000% higher, or lower, than the appropriate standard. Similarly, a significant difference may be detected when a parameter, level or value is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than the level of the appropriate standard. Significant differences may be identified by using an appropriate statistical test. Tests for statistical significance are well known in the art and are exemplified in Applied Statistics for Engineers and Scientists by Petruccelli, Chen and Nandram Reprint Ed. Prentice Hall (1999).

Figures 11A, 11B:
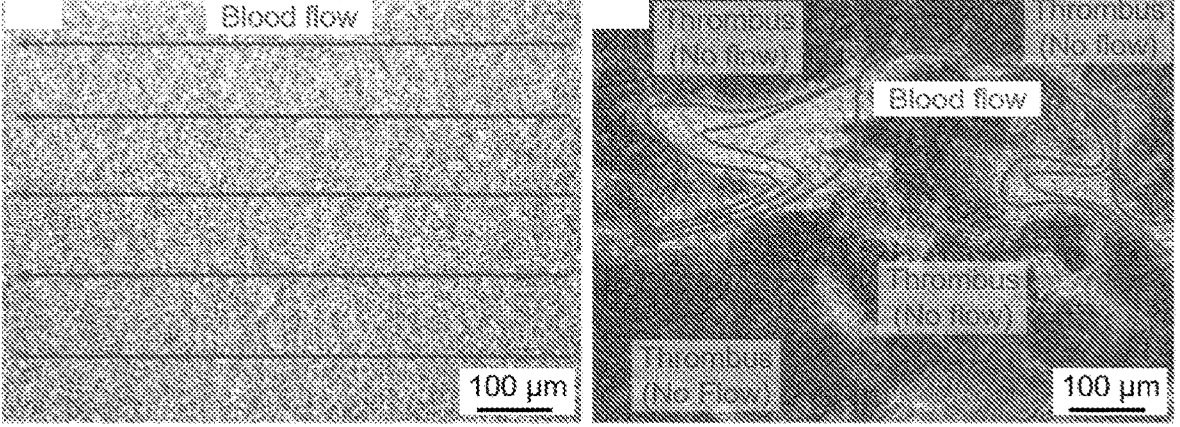
FIGS. 11A-B illustrate thrombin-induced thrombus formation in a microchannel. (A) No thrombus formation in a microchannel perfused with citrate whole blood reconstituted with 16.7 μM calcium chloride, and blood flows uniformly in the microfluidic channel. (B) Thrombus formation in a microchannel perfused with same citrate whole blood reconstituted with 16.7 μM calcium chloride and 5 UI/mL human alpha thrombin. Blood flow was completely blocked by the formed thrombi.

By way of example, to demonstrate the imaging velocimetry technique, two blood samples were tested. A "control" case of whole blood with no additives, and a second case with an addition of 100 mM calcium chloride solution to enhance clotting. FIG. 11 shows two types of data that can be derived from the blood images. First, the temporal evolution of the mean flow velocity determined by PIV which allows the calculation of the clotting time and decay rate, and second a detailed view of the blood flow velocity field using wOFV with both the velocity magnitude and streamlines visualized. Computation of the streamlines, enabled by wOFV, allows both the identification of primary blood flow channels around thrombi and the ability to track them over time.

In some embodiments, data on the measurement blood flow velocity can be used in combination with data on the velocity and/or velocimetry of blood flow in the microchannel under normoxia or hypoxia. The data obtained can include a value for the velocity for one of the cells in the blood or the average velocity for a population of cells, the distance traveled by one of the cells, the time for one of the cells to travel a certain distance, the average distance traveled by a population of the cells, or the average time for a population of the cells to travel a certain distance in the microchannel. The data on velocity and/or viscosity can be developed from one or more simulations of blood flow using PIV or wOFV.

In some embodiments, the microfluidic system can be used in a method of determining a subject having a vaso-occlusive crises (VOC). The method can include obtaining blood from the subject and perfusing the blood containing through the microfluidic channel that optionally includes various capturing agents, such as E-Selectin, P-Selectin, ICAM-1, VCAM-1, and/or endothelial cells, provided in or functionalized to the microchannels. The blood flow viscosity and/or coagulation of the blood as well as adhesion of blood cells, such as RBCs and WBCs, to the various capturing agents provided in or functionalized to the microchannels of the microfluidic device can then be determined and compared to a standard or control.

Other embodiments described herein relate to a method for identifying the effectiveness of a candidate therapeutic agent for treating a condition or disease in a subject. The method can include obtaining blood, from a subject suspected of having or a risk of a disorder, and perfusing the blood in the presence of the therapeutic agent through the microfluidic channel that optionally includes various capturing agents, such as E-Selectin, P-Selectin, ICAM-1, VCAM-1, and/or endothelial cells, provided in the microchannels. The candidate therapeutic agent can be administered the blood prior to perfusing the blood through microchannel and/or to the microchannel and/or after formation of thrombi or clots in the microchannel. The thrombi or clot formation in the microchannel in the presence of the therapeutic agent can compared with control or standard to determine the effectiveness of the therapeutic agent. In some embodiments, the perfusion of the blood can occur under normoxia or hypoxia conditions.

Other embodiments described herein relate to a method for determining the effectiveness of a therapeutic agent for treating a condition or disease in a subject. The method can include obtaining from a subject suspected of having or a risk of a disorder, and perfusing the blood in the presence of the therapeutic agent through the microfluidic channel that optionally includes various capturing agents, such as E-Selectin, P-Selectin, ICAM-1, VCAM-1, and/or endothelial cells, provided in the microchannels. The therapeutic agent can be administered to the blood prior to perfusing the blood through the microchannel and/or to the microchannel and/or after formation of thrombi or clots in the microchannel. The thrombi or clot formation in the microchannel in the presence of the therapeutic agent can compared with control or standard to determine the effectiveness of the therapeutic agent. In some embodiments, the perfusion of the blood can occur under normoxia or hypoxia condition.

Example 1

This example describes a microfluidic platform integrated with both particle image velocimetry (PIV) and wavelet-based optical flow velocimetry (wOFV) processing to monitor changes in whole blood rheology as well as spatiotemporal variations in local blood velocity, respectively, during coagulation. The flow is imaged using volumetric illumination with a simple experimental setup. The images are path-integrated through the height of the microchannel, so velocimetry yields the average velocity over that height. The flow and coagulation dynamics are primarily two-dimensional, however, so the path integration does not present significant practical limitations. Moreover, microscopic images of the flow field allow thrombus growth to be quantified over time, in relation to the local and average flow velocities. These parameters are expected to demonstrate a unique behavior from a clinical perspective, in which people with clotting disorders may present abnormal thrombus growth rate and associated blood flow dynamics, which will be a function of total pressure drop and the shape of thrombus. The microfluidic approach described here may also be utilized to evaluate the effect of emerging therapeutic approaches on clotting dynamics and thrombus formation.

Experimental Setup

Figure 2:
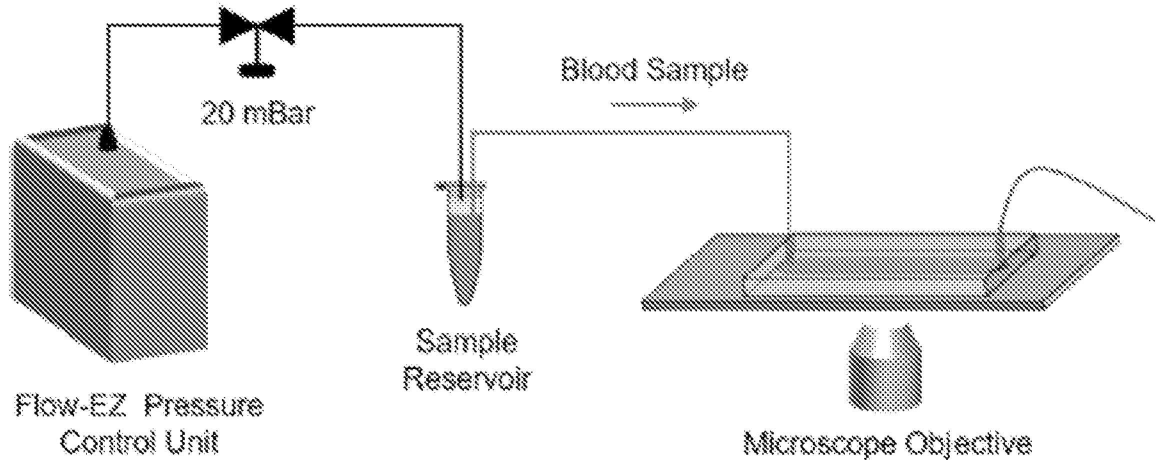
FIG. 2 is a schematic view of the experimental setup. A pressure control unit was utilized to inject the blood sample into the microfluidic channel at a constant pressure of 20 mBar. The microfluidic channel was placed on an inverted microscope, and the blood flow was recorded under 4× magnification using a high-resolution microscope camera.

The whole blood sample for this example was drawn into a 3.2% sodium citrate containing vacutainer from a single healthy donor under an Institutional review board-approved protocol. The blood sample was stored at 4° C. upon collection and was processed within 24 h. Briefly, a double-sided adhesive and a polymethyl methacrylate top cover were laser micromachined and then assembled with a standard microscope glass slide. The microchannel dimensions defined by the double-sided adhesive are 4×25×0.05 mm (width×length×height). The assembled microchannels were washed with phosphate-buffered saline (PBS, 1X) and absolute ethanol (100%), which was followed by tubing assembly. To induce blood coagulation, a $CaCl_2$ stock solution was prepared by dissolving calcium chloride dehydrate in PBS at a concentration of 600 mM. Prior to the experiment, the whole blood sample was recalcified with the stock solution to obtain a final concentration of 100 mM $CaCl_2$. Although a $CaCl_2$ concentration of 100 mM is relatively high compared to the physiological range, calcium concentration does not significantly change coagulation time after a certain level. We decided to use a high level of calcium concentration to ensure proper coagulation of Na-citrate containing blood sample for this proof-of-concept study. The control experiment was performed by mixing the whole blood sample with PBS. Thereafter, the mixed blood sample was immediately injected into the microfluidic channel at a constant inlet pressure of 20 mBar by means of a Flow-EZ pressure control unit (Fluigent Inc., North Chelmsford, MA), as shown in FIG. 2. The constant supply pressure implies that the flow rate is reduced as the blood coagulates. The maximum initial shear rate was approximately 10 $s^{-1}$, and the shear rate reduced to zero as the flow slowed and eventually stopped due to microchannel blockage as coagulation occurred. The microfluidic channel was placed on an inverted microscope (Olympus IX83), and a video was recorded simultaneously under 4× magnification using a high-resolution camera (EXi Blue EXI-BLU-R-F-M-14-C) at 10 frames per second as soon as the flow was started. The field of view was centered on the microfluidic channel, and one pixel in the images corresponds to 1.58 μm.

Results

As stated previously, two sets of images from different experiments are considered in this example. For both cases, the entire image sequence is first processed using a state of the art commercial PIV code (TSI Inc. Insight 4G) to determine the bulk properties of the blood flow and observe averaged trends over time. wOFV is then applied to later images in the 100 mM $CaCl_2$ case to demonstrate a detailed analysis of the coagulation dynamics.

Figure 3:
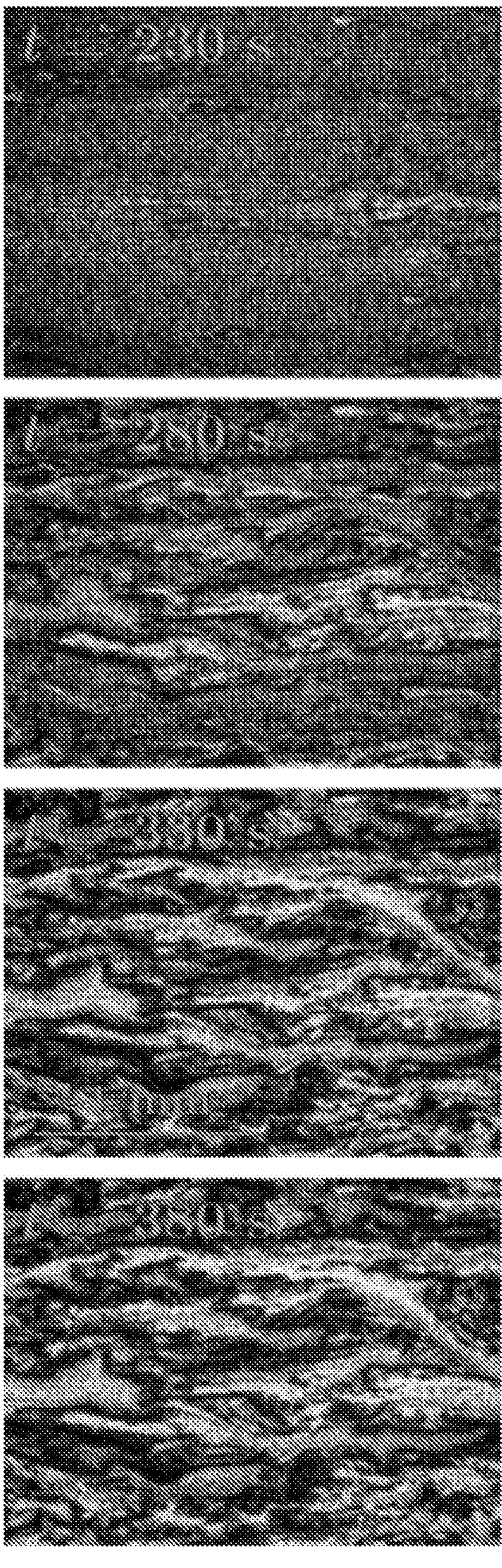
FIG. 3 illustrates an example blood flow images from the 100 mM $CaCl_2$ case at t=230-380 s at intervals of 50 s, showing the development of coagulation. Flow is from left to right. The flow has coagulated in the dark regions of the bottom three images. The images have been preprocessed using the steps described in the text. The horizontal line in the lower left of the image at t=330 s indicates the scale (1 mm).

An example blood flow image for the 100 mM $CaCl_2$ case after spontaneous clots have formed through the microchannel is shown in FIG. 3. The flow is from left to right. The images are preprocessed prior to performing velocimetry with three preprocessing steps: first, mean filtering with a 3 3-pixel kernel, followed by intensity normalization and finally edge-aware local Laplacian filtering to enhance contrast. The mean filtering reduces imaging noise while the other two processes improve motion estimation from the images. Individual red blood cells (erythrocytes) appear as small dots in the image, creating a speckle-like pattern. The erythrocytes are used by both PIV and wOFV as flow tracers to estimate velocity.

Particle Image Velocimetry Analysis

Figure 4:
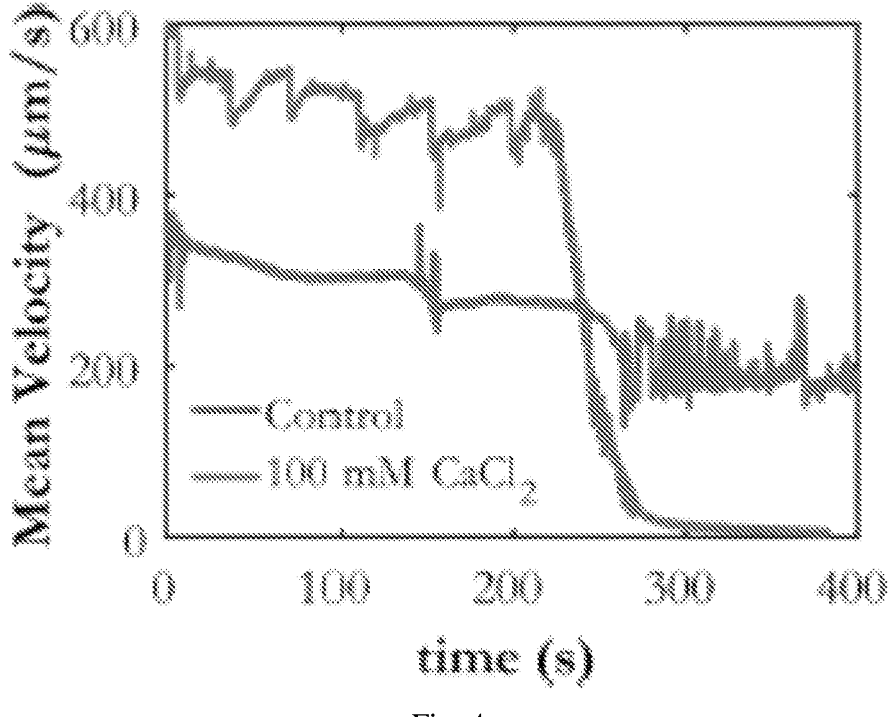
FIG. 4 illustrates a plot showing mean horizontal velocity for each case determined by PIV. The clotting time is observed to be 220 s.

Particle image velocimetry analysis was performed for both cases using Insight 4 G. The algorithm used multiple passes with grid deformation, starting with 128-high 192-wide pixel interrogation spots and moving to a final spot size of 32×64 pixels. The initial and final interrogation spots are overlapped by 50% in both directions, so the spacing between PIV vectors is 25.28 and 50.56 μm in the spanwise and streamwise directions, respectively. FIG. 4 shows the horizontal component of velocity averaged over the image domain for both cases as a function of time. The difference in mean velocity at t=0 s between the cases is due primarily to the $CaCl_2$ content in the 100 mM $CaCl_2$ case, which lowers its viscosity, increasing the velocity for the same driving pressure. Note that while the bulk velocity for the control case is relatively constant over the entire 400-second image sequence, indicating minimal activation of the coagulation cascade, the 100 mM $CaCl_2$ case shows a dramatic drop in velocity around t=220 s corresponding to the formation of large thrombi made up of heterotypic cellular aggregates that are visible under the micro-scope (FIG. 3). We postulate that this large drop in mean blood flow velocity is indicative of clotting time, during which the resistance inside the microchannel significantly increases because of thrombus formation, thereby slowing down the flow. Some noise is apparent in both time traces, but it is likely random and can be smoothed out to determine global trends such as the velocity decay rate, which could be calculated between t=220 s and when the average velocity becomes relatively constant again, around t=300 s. The increased noise in the control case beginning around t 270 s is likely due to the presence of small thrombi in the image domain which cause errors in the PIV processing.

An important factor for the accuracy of both PIV and wOFV is the displacement of the flow tracers between consecutive frames, or the interframe displacement. The accepted rule of thumb for PIV processing is that the maximum interframe displacement should be less than one quarter of the size of the largest interrogation spot. For wOFV, peak accuracy for particle images occurs for displacements of less than about five pixels. The factor between interframe displacement and velocity in μm/s is 15.8, i.e., a displacement of one pixel corresponds to a velocity of 15.8 μm/s. Referencing FIG. 4, the interframe displacement prior to coagulation in the 100 mM $CaCl_2$ case is 30-35 pixels, which is suitable for PIV processing and the selected interrogation spot size according to the aforementioned rule of thumb. It is much too large for wOFV processing, however, and wOFV does not become accurate until the maximum velocity at a given time drops below 80 μm/s. The average velocity meets this threshold at about t=260 s, but the maximum velocity in the image domain at a given time instance does not drop below 80 μm/s until much later, around 320 s.

Wavelet-Based Optical Flow Velocimetry Analysis

Wavelet-based optical flow velocimetry was applied to images from the 100 mM $CaCl_2$ case toward the end of the sequence when coagulation has reduced the flow velocity, from t=280 s to t 380 s. The optimal value of the regularization parameter in Eq. (3) was determined to be $k{\times}10^{-1:8}$. Two important features of the flow under consideration in this example in the context of wOFV are that (1) the flow is incompressible, and (2) the flow is entirely two-dimensional. As a result, the accuracy of wOFV can be enhanced substantially by projecting the estimated velocity field to divergence free space via a Helmholtz decomposition. This can be done because not only is the true flow divergence-free (because it is incompressible), but there is no apparent divergence in the images due to out-of-plane velocity. Increasing the accuracy of OFV methods by employing a Helmholtz decomposition is used extensively when assessing their accuracy with syn-thetic data from incompressible, two-dimensional flows.

Furthermore, incompressibility and two-dimensionality can be exploited to a greater degree in wOFV methods in particular, where the velocity can be restricted to divergence-free space during computation by using divergence-free wavelet bases. This is not implemented in this study and is left for future work, but the estimated flow is projected to divergence-free space after computation via Helmholtz decomposition here.

Figure 5A:
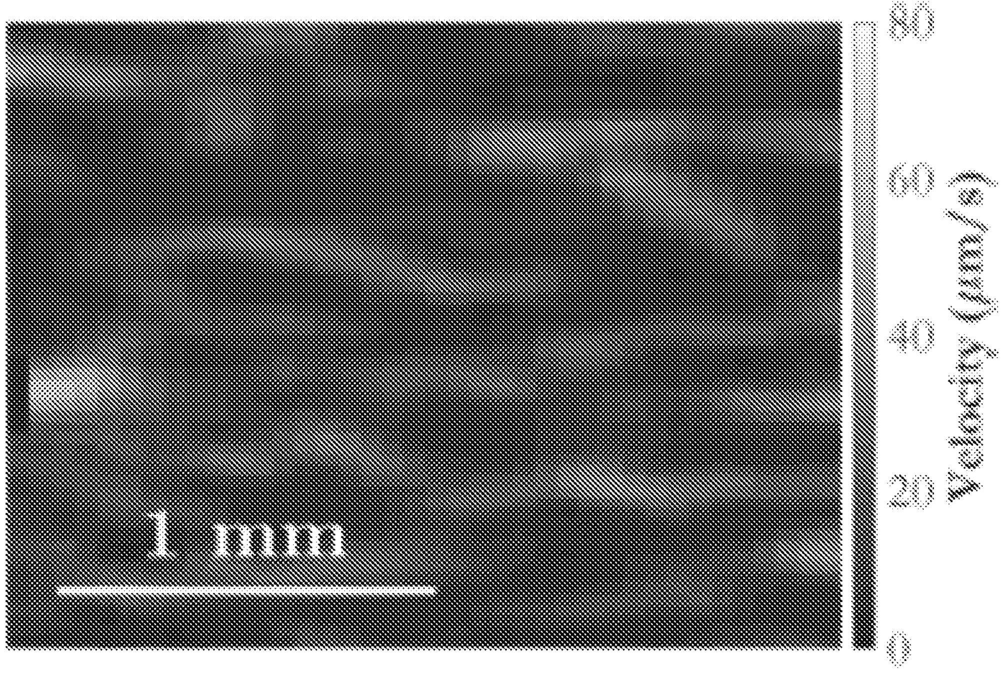
FIGS. 5(A-B) illustrate instantaneous snapshots of the velocity field at t=330 s for (a) PIV and (b) wOFV. The velocity field is colored according to velocity magnitude, and the spatial scale is shown in the lower left of each subfigure.
Figure 5B:
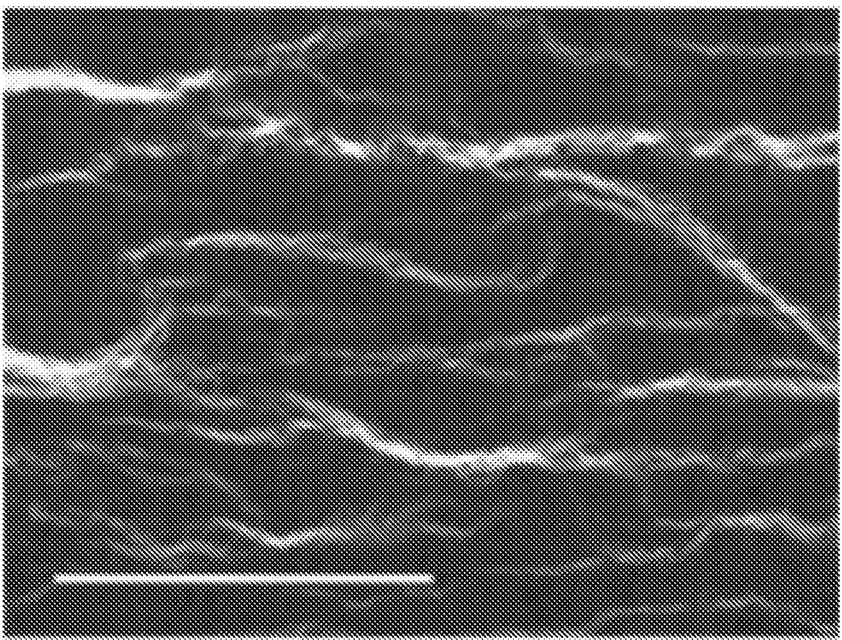

The results in this section are intended to give a flavor of the kind of information that can be extracted from blood flow images using wOFV, and indicate the types of analyses that could be performed to foster new insights regarding blood flow and coagulation dynamics FIG. 5 shows an example instantaneous snapshot of the magnitude of the velocity field at t=330 s for PIV and wOFV. One can immediately see the dramatic increase in the amount of detail afforded by wOFV due to its much finer spatial resolution. The vector spacing for wOFV is the same as the pixel spacing, or 1.58 μm. The thrombi grow during the coagulation process, so the length scales in the problem evolve, shrinking in time. From the data shown in FIG. 4, at t=330 s, the length scales of the thrombi appear to be of the order of tens to hundreds of microns. Additionally, it is apparent from manual inspection of the image pair for the velocity field in FIG. 5 that PIV is underestimating the displacements, while wOFV is capturing them accurately. This is likely due both to wOFV being better suited to natural images than PIV, and because of the sharp spatial velocity gradients on the border of the flow channels that have formed around the thrombi.

Figure 6A:
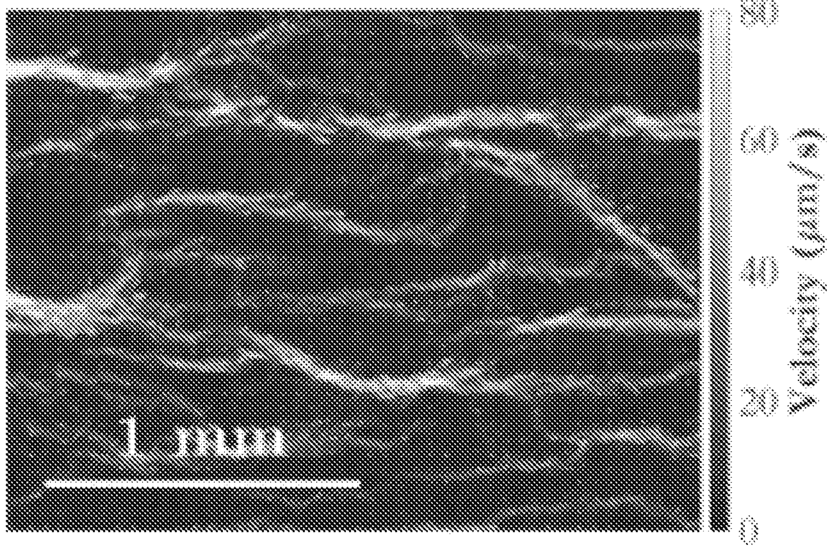
FIGS. 6(A-B) illustrates instantaneous snapshots of the velocity field at t=330 s for wOFV showing (A) velocity vectors and (B) streamlines. The velocity field is colored according to velocity magnitude. Velocity vectors are subsampled by a factor of 30 in both dimensions and scaled by a factor of 20 to aid in visualization. The transparency for each streamline is set according to the mean residence time along that streamline, with more transparency indicating a longer residence time (lower average velocity). The vertical white line in (B) is referenced in FIG. 7. The horizontal white lines indicate the spatial scale. A zoomed-in image of the region marked by a red rectangle in (B) shows the streamlines in finer detail.

As a first step in further analysis of the wOFV results, velocity vectors are superimposed on the velocity field in FIG. 6(A). The vectors complement the velocity magnitude data by giving an indication of flow direction. Alternative flow markers, which are even more informative, are the streamlines shown in FIG. 6(B).

Figure 6B:
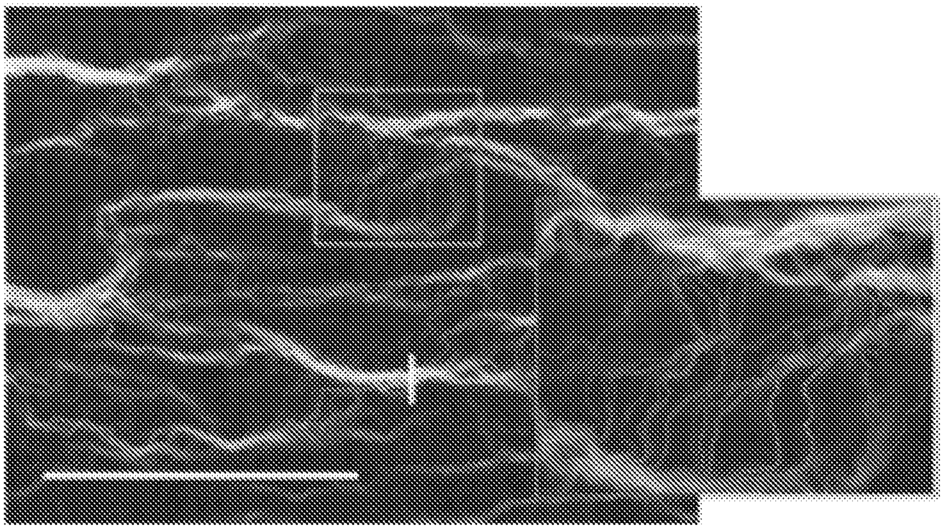

Streamlines are curves that are everywhere tangent to the local flow velocity. They are calculated by seeding the velocity field at starting locations along the left and right borders of the domain, and then marching parametrically from those locations in space according to the velocity field. Streamlines from starting locations seeded at the right edge of the domain are computed by marching backward, i.e., using v instead of v. A total of 520 equally spaced starting locations are seeded on each side of the domain, for a total number of 1040 potential streamlines. The high spatial resolution afforded by wOFV allows the streamlines to be computed accurately from the velocity field at each instant in time. Not all starting locations will yield a streamline which traverses the domain, however, and only streamlines, which do so are shown in FIG. 6(B). Other streamlines, which are the ones seeded into locations where there are no flow channels, i.e., inside of thrombi, do not propagate from their initial locations because the local flow velocity is zero.

The transparency of the streamlines in FIG. 6 represents the residence time of a fluid element (or a single erythrocyte) along that streamline, normalized by the length of the streamline FIG. 7 shows a histogram, normalized as a probability density function, of normalized residence times for the streamlines in FIG. 6(B). The streamlines with a shorter normalized residence time correspond to higher average velocity along a flow path, indicating a higher flow rate of erythrocytes. It is possible that the residence time of a streamline may have some use in predicting which channels are more likely to close due to coagulation.

A more rigorous analysis of this type would use pathlines instead of streamlines, because pathlines explicitly follow Lagrangian fluid elements instead of being tangent to the local velocity. For steady flows, pathlines and streamlines coincide. The flow in this example is steady enough over the timescale of a fluid element traversing the image domain in one of the faster-moving channels that those streamlines and pathlines would be very similar, but FIG. 7 indicates that the median time for a fluid element to traverse the 2.2 mm-long domain is of the order of 150-200 s, so some features of the flow field certainly change over that time interval. Pathlines are more difficult to compute than streamlines, however, because they require good temporal resolution of the evolving velocity field, which is why they are not computed here. Nonetheless, the investigation of local flow properties along path-lines would likely be a worthwhile avenue to pursue with more highly resolved data.

Further quantitative information can be extracted from the temporal evolution of the velocity field and streamlines FIG. 8(A) shows a quantity designated as the blockage ratio as a function of time. In this work, the blockage ratio is defined as the number of streamlines that traverse a significant portion of the domain divided by the total number of seeded streamline starting locations. For instance, at t=320 s, the blockage ratio is about 0.5, indicating that 50% of the starting locations along the left and right edges of the velocity field yield a valid streamline; that is, one that traverses the domain. The blockage ratio defined this way is expected to closely approximate the fraction of the cross-sectional area of the channel that remains open to blood flow.

Figure 9:
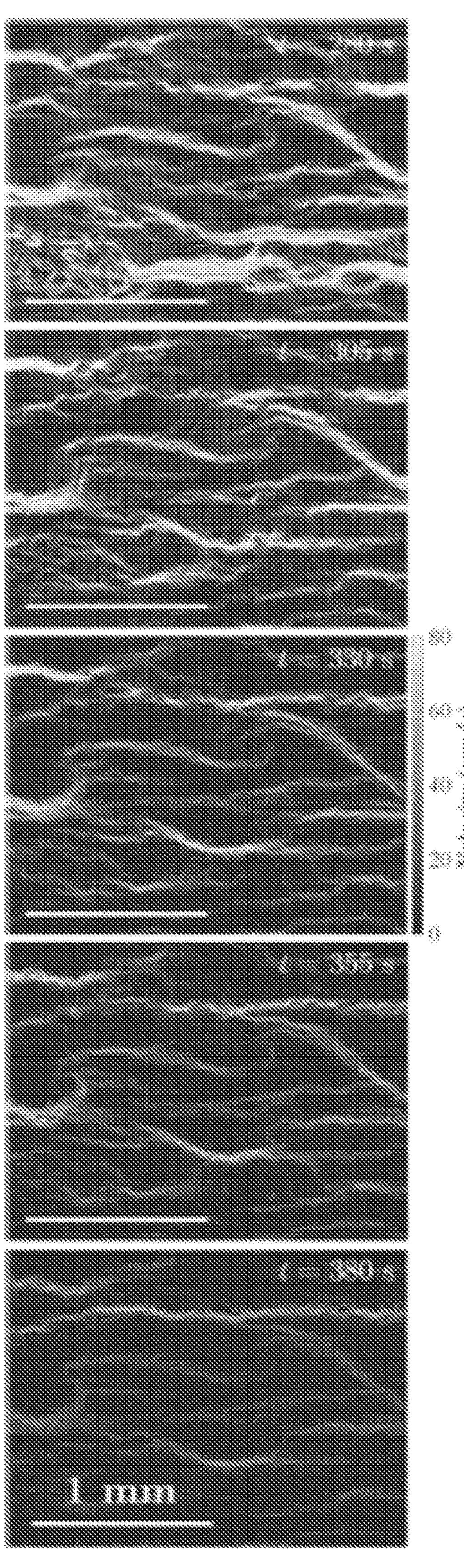
FIG. 9 illustrates images showing evolution of the velocity field determined using wOFV as a function of time. Coloration indicates velocity magnitude, and the streamlines are colored according to mean residence time. Horizontal white lines indicate the spatial scale.

FIG. 8(B) shows the evolution of profiles of the horizontal component of velocity, sampled along the vertical white line in FIG. 6(B). Each profile is averaged over 5 consecutive temporal snapshots, or 0.5 s, to reduce noise. The reduction in velocity in the flow channel as a function of time can be clearly observed, beginning between t=354 s and t=366 s. Using data from wOFV processing, future studies can analyze the velocity profile evolution in isolated flow channels to investigate coagulation dynamics Finally, FIG. 9 gives a global view of the temporal evolution of the velocity field. Not only can the connections between primary flow channels be observed at a single instant, but one can track how a given channel changes in time. These changes might include shape, width, velocity, or its relationship with other flow passages. The entire sequence of velocity fields can readily be converted into a movie, which can be played simultaneously with a movie of the recorded images. The videos can be studied to identify regions of interest for further analysis.

As an example, a particular feature of interest in FIG. 9 is the long, wide channel of high-velocity flow toward the bottom center of the frame at t=280 s (top image). It appears to conduct a significant amount of flow, and the erythrocytes are fast-moving, so intuitively one might not expect coagulation to occur in that location. Yet, by t=305 s, the flow in that region has significantly diminished and by t=330 s the channel has almost completely disappeared, indicating thrombus formation. The reason for this can be observed in the top two frames in FIG. 9. The large channel occupies about two thirds of the width of the frame on the right-hand side, but the velocity field at t=280 s reveals that it is fed by a complex network of a large number of small, low-velocity channels on the left-hand side of the domain. This network experienced coagulation shortly after t=280 s, and as that region begins to clot, the flow feeding the large channel is choked off. The velocity in the large channel decreases rapidly as the channel is deprived of its supply, allowing a thrombus to form. Observations from FIG. 9 indicate that the rapid increase in blockage ratio observed in FIG. 8(A) between t=280 s and t=320 s is primarily due to the obstruction of this particular large channel.

Particle image velocimetry and wOFV have been applied for the first time to a series of microscopic images of whole blood flow in a microchannel during coagulation. Each method offers its own set of strengths, depending on the details of the experiment and the desired data to be acquired. PIV is well suited to compute average velocity over the entire image domain, particularly when the interframe displacements are larger than five pixels, but it fails to accurately capture fine flow features as the blood begins to coagulate. wOFV, on the other hand, offers orders of magnitude higher spatial resolution and is well-suited to determining velocity from natural images, such as the erythrocytes in whole blood.

This enables much more detailed investigations of the flow field evolution during coagulation, potentially offering new insights into coagulation dynamics in future work.

The microfluidic system integrated with PIV and wOFV described in this example holds great promise for potential future applications from a clinical perspective. For example, assessment of clotting time and decay rate for a clinically diverse patient population can enable monitoring of disease status and the impact of therapeutical interventions on variations in these parameters. More importantly, functionalization of microchannel surface via relevant biological substrates (e.g., heparin, thrombin, Factor XII, etc.) may alter fluid dynamics and thrombus formation in a patient-specific fashion and warrants further research. Further, the efficacy of emerging therapies against thrombus-targeting fibrinolysis can be quantitatively evaluated under physiologically relevant shear conditions using this approach.

Example 2

The preliminary results in Example 1 support the hypothesis that coagulation disorders and therapies have observable, quantifiable impacts on the properties of coagulation. Furthermore, they demonstrate that wOFV analysis shows the coagulation process can be entirely characterized and predicted by knowledge of the fluid dynamics.

Example 1 demonstrates that continuous imaging at 10 Hz is not sufficient to resolve the flow velocity at early times, prior to and during the onset of coagulation, with wOFV. Therefore, we propose to record images with a two-camera system instead of a single camera. FIG. 10 shows the proposed two-camera system. Instead of attaching the camera directly to the microscope objective, a unit containing a 50/50 beamsplitter is attached to the objective. Two identical cameras are then attached to the beamsplitter unit by conventional camera mounts, such that each camera has an identical view of the scene transmitted from the microscope. Both cameras operate at a continuous framing rate of e.g., 10 Hz, but they are triggered such that Camera 2 acquires its images a short time Δt after the images acquired by Camera 1. By specifying Δt, the user can precisely control the inter-frame displacement of the observed blood flow between Cameras 1 and 2. Instead of comparing image N with image N+1 from the same camera to determine the velocity as in example 1, we will instead compare image N from Camera 1 to image N from Camera 2. In order to produce accurate results, the two cameras must be carefully aligned such that their fields of view are as identical as possible. This will be achieved first by incorporating a combination of bellows and micrometer-adjustment stages to the beamsplitter unit such that the relative camera positions can be finely adjusted. Second, we have developed an image registration routine in MATLAB which creates a transformation to register one image onto another from a different camera, which will be used to correct any slight misalignments during post-processing after the images have been acquired.

Wavelet-based optical flow velocimetry (wOFV) will be used to determine the velocity of the blood flow from image pairs acquired from the two cameras shown in FIG. 10. Example 1 demonstrates that the improved spatial resolution and accuracy of wOFV relative to PIV are necessary to obtain the fine-scale dynamics of the flow during coagulation. In order to enhance the accuracy of wOFV further, an algorithm can be used which exploits the two-dimensional nature of the microchannel flow under investigation. Specifically, because the flow is incompressible and very nearly two-dimensional, the velocity field in the imaging plane is divergence-free. The properties of the separable wavelet transforms embedded in the wOFV algorithm allow a zero-divergence constraint to be placed on the calculated velocity field during computation, i.e., the velocity field produced by wOFV is divergence-free by construction.

Interactions between blood flow and hemostasis in healthy individuals can be thoroughly investigated using the system and methods outlined above. Blood samples from several healthy donors can be used to determine the natural variability in coagulation dynamics between individuals. wOFV analysis will be used to determine the velocity field during initial thrombus formation and growth, which could not be captured due to the large inter-frame displacement in Example 1. From the high-resolution velocity data, important derivative quantities, such as vorticity and shear rate will be calculated, as will pathlines and streamlines A careful analysis of these data will be performed to build a predictive model of thrombus formation and growth based on the flow parameters that are determined to be important. The predictive model can be verified using other blood samples from healthy patients. Thrombus formation inside the microfluidic channels can be triggered via re-calcification of the anticoagulated blood samples and by functionalization of the microchannel surface using procoagulant molecules (e.g., thrombin, collagen, Factor XII, etc.). The microchannel surfaces will be functionalized with cultured human endothelial cells prior to the coagulation experiments to create a more physiologically-relevant milieu.

The influence of clotting disorders and therapies can be assessed in a case study using elevated levels of thrombin to promote coagulation. We have experience performing experiments in microchannels using whole blood with added thrombin (FIG. 11), demonstrating a marked increase in the coagulation rate. It is hypothesized that elevated levels of thrombin will produce distinctive, quantifiable effects on the evolution of the blood flow and the associated formation and growth of thrombi, and these experiments will allow us to assess the ability of our model to identify those effects. Additionally, the effect of heparin, a common anticoagulant therapy, on the blood flow will be evaluated by adding heparin into the blood samples at appropriate doses.

In addition to these controlled experiments involving blood from healthy patients with added thrombin, we can perform a set of experiments using blood from a small set of patients with severe sepsis who have experienced or are experiencing capillary thrombosis. Real disease states are significantly more complex than an elevated level of a single clotting factor or protein in otherwise healthy blood, so it is important to study the blood flow dynamics in blood from diseased patients rather than attempting to simulate the pathological changes to the blood. Distinguishing the characteristics of blood flow in patients with sepsis and capillary thrombosis from those in patients with healthy blood could potentially enable new clinical diagnostic approaches and therapies to prevent thrombosis in sepsis patients.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A system comprising:

a microfluidic device having at least one microchannel through which a blood sample flows;

a camera configured to obtain a plurality of images of the blood sample flowing through the microchannel; and a processor configured to determine one or more hemodynamic parameters based on differences between two sets of consecutive images of the plurality of images, wherein the processor uses particle image velocimetry (PIV) of a first set of consecutive images to determine temporal evolution of mean blood flow velocity and wavelet-based optical flow velocimetry (wOFV) of a second set of consecutive images to determine a blood flow velocity field, and wherein the processor is configured to identify blood flow channels around thrombi formed in the microchannel by the blood flow velocity field generated by wOFV.

2. The system of claim 1, wherein the PIV and wOFV use images of individual blood cells of the flowing blood sample as flow tracers to estimate velocity.

3. The system of claim 1, wherein the processor is configured to calculate clotting time and decay rate based on the temporal evolution of the mean flow velocity.

4. The system of claim 1, wherein the processor is configured to pre-process the images prior to PIV and wOFV, wherein the pre-processing includes mean filtering intensity normalization, and edge-aware Laplacian filtering.

5. The system of claim 4, wherein the mean filtering reduces image noise and the intensity normalization and edge-aware Laplacian filtering improve motion estimation of the images.

6. The system of claim 1, wherein the processor is configured to segment a first image and a second image of the first set of images into a plurality of interrogation regions, cross-correlate each of the plurality of interrogation regions, and identify one more velocity vectors based on the cross-correlated interrogation regions for PIV.

7. The system of claim 1, wherein the processor is configured to superimpose velocity vectors or streamlines on the blood flow velocity field determined by wOFV to determine residence time of a blood cell along flow path in the microchannel.

8. The system of claim 1, channel having at least one functionalized adhesion region adapted to adhere to blood cells of interest within the blood sample.

9. The system of claim 1, comprising at least two cameras that provide staggered image acquisition of the blood flowing through the microchannel.

10. The system of claim 9, wherein two cameras are attached to a beamsplitter unit, such that each camera has an identical view of the microchannel, wherein both cameras operate at continuous framing but are triggered such that the second camera acquires its images a time Δt after the images acquired by the first camera, and wherein the processor compares images from the first camera to images of the second camera.

11. A method of determining one or more hemodynamics of a blood sample, the method comprising:

obtaining a plurality of images of the blood sample flowing through a microchannel of a microfluidic device; and determining one or more hemodynamic parameters based on differences between two sets of consecutive images of the plurality of images, wherein a processor uses particle image velocimetry (PIV) processing of a first set of consecutive images to determine temporal evolution of mean blood flow velocity and wavelet-based optical flow velocimetry (wOFV) processing of the second set of consecutive images to determine a blood flow velocity field; and identifying blood flow channels around thrombi formed in the microchannels by the blood flow velocity field generated by wOFV.

12. The method of claim 11, further estimating flow velocity for the PIV and wOFV by identifying individual blood cells of the flowing blood sample.

13. The method of claim 11, further comprising calculating clotting time and decay rate based on the temporal evolution of the mean flow velocity determined by PIV.

14. The method of claim 12, further applying one of mean filtering, intensity normalization, and edge-aware Laplacian filtering to the images prior to PIV and/or wOFV.

15. The method of claim 11, further comprising segmenting a first image and a second image of the first set of images into a plurality of interrogation regions, cross-correlating each of the plurality of interrogation regions, and identifying one more velocity vectors based on the cross-correlated interrogation regions for PIV.

16. The method of claim 11, further comprising superimposing velocity vectors or streamlines on the blood flow velocity field determined by wOFV to determine residence time of a blood cell along flow path in the microchannel.

17. The method of claim 11, wherein the microchannel has at least one functionalized adhesion region adapted to adhere to blood cells of interest within the blood sample.

18. The method of claim 11, wherein the plurality of images are obtained by two cameras that provide staggered image acquisition of the blood flowing through the microchannel, wherein both cameras operate at continuous framing but are triggered such that the second camera acquires its images a time Δt after the images acquired by the first camera.

19. The method of claim 18, further comprising comparing images from the first camera to images of the second camera.

* * * * *